US005830837A

United States Patent [19]

Bisgård-Frantzen et al.

[11] Patent Number: 5,830,837

[45] Date of Patent: Nov. 3, 1998

[54] AMYLASE VARIANTS

[75] Inventors: Henrik Bisgård-Frantzen, Lyngby; Torben Vedel Borchert, København; Allan Svendsen, Birkerød; Marianne Thellersen, Frederiksberg; Pia Van der Zee, Virum, all of Denmark

[73] Assignee: Novo Nordisk A/S, Bagsvaerd, Denmark

[21] Appl. No.: 343,804

[22] Filed: Nov. 22, 1994

[51] Int. Cl.[6] .......... C12N 9/28

[52] U.S. Cl. .......... 510/226; 510/392; 435/202; 435/203; 435/204; 435/69.1; 435/252.3; 435/320.1; 536/23.1; 536/23.7

[58] Field of Search .......... 435/6, 252.3, 69.1, 435/832, 202, 320.1; 424/94.61; 536/23.2, 23.7; 510/226, 392

[56] References Cited

U.S. PATENT DOCUMENTS

| | | | |
|---|---|---|---|
| 5,093,257 | 3/1992 | Gray | 435/202 |
| 5,093,325 | 3/1992 | Gray | 435/202 |

FOREIGN PATENT DOCUMENTS

| | | |
|---|---|---|
| 252666 | 1/1988 | European Pat. Off. . |
| 285123 | 3/1988 | European Pat. Off. . |
| 0285123 | 10/1988 | European Pat. Off. . |
| 368341 | 5/1990 | European Pat. Off. . |
| 525610 | 2/1993 | European Pat. Off. . |
| 2676456 | 11/1992 | France . |
| 91/003533 | 1/1991 | WIPO . |
| WO 91/00353 | 1/1991 | WIPO . |
| WO 94/02597 | 3/1994 | WIPO . |
| WO 94/14951 | 7/1994 | WIPO . |
| WO 94/18314 | 8/1994 | WIPO . |

OTHER PUBLICATIONS

Suzuki et al., J. of Biol. Chem., vol. 264, No. 32, pp. 18933–18938 (1989).

Suzuki et al. J. Biol. Chem. (1989), 264(32):18933–18938, Nov. 15, 1989.

*Primary Examiner*—Robert A. Wax
*Assistant Examiner*—Tekchand Saidha
*Attorney, Agent, or Firm*—Steve T. Zelson, Esq.; Cheryl H. Agris, Esq.

[57] ABSTRACT

A variant of a parent α-amylase enzyme having an improved washing and/or dishwashing performance as compared to the parent enzyme, wherein one or more amino acid residues of the parent enzyme have been replaced by a different amino acid residue and/or wherein one or more amino acid residues of the parent α-amylase have been deleted and/or wherein one or more amino acid residues have been added to the parent α-amylase enzyme, provided that the variant is different from one in which the methionine residue in position 197 of a parent *B. licheniformis* α-amylase has been replaced by alanine or threonine, as the only modification being made. The variant may be used for washing and dishwashing.

42 Claims, 12 Drawing Sheets

SEQUENCE LISTING ( 1 ) GENERAL INFORMATION:

( i i i ) NUMBER OF SEQUENCES: 38

( 2 ) INFORMATION FOR SEQ ID NO:1:

-continued ( i ) SEQUENCE CHARACTERISTICS:
( A ) LENGTH: 1920 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 334..1872

( i x ) FEATURE:
( A ) NAME/KEY: sig_peptide
( B ) LOCATION: 334..420

( i x ) FEATURE:
( A ) NAME/KEY: mat_peptide
( B ) LOCATION: 421..1869

( x i ) SEQUENCE DESCRIPTION: SEQ ID NO:1:

CGGAAGATTG GAAGTACAAA AATAAGCAAA AGATTGTCAA TCATGTCATG AGCCATGCGG 60

GAGACGGAAA AATCGTCTTA ATGCACGATA TTTATGCAAC GTTCGCAGAT GCTGCTGAAG 120

AGATTATTAA AAAGCTGAAA GCAAAAGGCT ATCAATTGGT AACTGTATCT CAGCTTGAAG 180

AAGTGAAGAA GCAGAGAGGC TATTGAATAA ATGAGTAGAA GCGCCATATC GGCGCTTTTC 240

TTTTGGAAGA AAATATAGGG AAAATGGTAC TTGTTAAAAA TTCGGAATAT TTATACAACA 300

TCATATGTTT CACATTGAAA GGGGAGGAGA ATC ATG AAA CAA CAA AAA CGG CTT 354
Met Lys Gln Gln Lys Arg Leu
-29 -25

TAC GCC CGA TTG CTG ACG CTG TTA TTT GCG CTC ATC TTC TTG CTG CCT 402
Tyr Ala Arg Leu Leu Thr Leu Leu Phe Ala Leu Ile Phe Leu Leu Pro
-20 -15 -10

CAT TCT GCA GCA GCG GCG GCA AAT CTT AAT GGG ACG CTG ATG CAG TAT 450
His Ser Ala Ala Ala Ala Ala Asn Leu Asn Gly Thr Leu Met Gln Tyr
-5 1 5 10

TTT GAA TGG TAC ATG CCC AAT GAC GGC CAA CAT TGG AGG CGT TTG CAA 498
Phe Glu Trp Tyr Met Pro Asn Asp Gly Gln His Trp Arg Arg Leu Gln
15 20 25

AAC GAC TCG GCA TAT TTG GCT GAA CAC GGT ATT ACT GCC GTC TGG ATT 546
Asn Asp Ser Ala Tyr Leu Ala Glu His Gly Ile Thr Ala Val Trp Ile
30 35 40

CCC CCG GCA TAT AAG GGA ACG AGC CAA GCG GAT GTG GGC TAC GGT GCT 594
Pro Pro Ala Tyr Lys Gly Thr Ser Gln Ala Asp Val Gly Tyr Gly Ala
45 50 55

TAC GAC CTT TAT GAT TTA GGG GAG TTT CAT CAA AAA GGG ACG GTT CGG 642
Tyr Asp Leu Tyr Asp Leu Gly Glu Phe His Gln Lys Gly Thr Val Arg
60 65 70

ACA AAG TAC GGC ACA AAA GGA GAG CTG CAA TCT GCG ATC AAA AGT CTT 690
Thr Lys Tyr Gly Thr Lys Gly Glu Leu Gln Ser Ala Ile Lys Ser Leu
75 80 85 90

CAT TCC CGC GAC ATT AAC GTT TAC GGG GAT GTG GTC ATC AAC CAC AAA 738
His Ser Arg Asp Ile Asn Val Tyr Gly Asp Val Val Ile Asn His Lys
95 100 105

GGC GGC GCT GAT GCG ACC GAA GAT GTA ACC GCG GTT GAA GTC GAT CCC 786
Gly Gly Ala Asp Ala Thr Glu Asp Val Thr Ala Val Glu Val Asp Pro
110 115 120

GCT GAC CGC AAC CGC GTA ATT TCA GGA GAA CAC CTA ATT AAA GCC TGG 834
Ala Asp Arg Asn Arg Val Ile Ser Gly Glu His Leu Ile Lys Ala Trp
125 130 135

ACA CAT TTT CAT TTT CCG GGG CGC GGC AGC ACA TAC AGC GAT TTT AAA 882
Thr His Phe His Phe Pro Gly Arg Gly Ser Thr Tyr Ser Asp Phe Lys
140 145 150

TGG CAT TGG TAC CAT TTT GAC GGA ACC GAT TGG GAC GAG TCC CGA AAG 930
Trp His Trp Tyr His Phe Asp Gly Thr Asp Trp Asp Glu Ser Arg Lys

-continued

```
155                 160                 165                 170

CTG AAC CGC ATC TAT AAG TTT CAA GGA AAG GCT TGG GAT TGG GAA GTT        978
Leu Asn Arg Ile Tyr Lys Phe Gln Gly Lys Ala Trp Asp Trp Glu Val
                175                 180                 185

TCC AAT GAA AAC GGC AAC TAT GAT TAT TTG ATG TAT GCC GAC ATC GAT       1026
Ser Asn Glu Asn Gly Asn Tyr Asp Tyr Leu Met Tyr Ala Asp Ile Asp
            190                 195                 200

TAT GAC CAT CCT GAT GTC GCA GCA GAA ATT AAG AGA TGG GGC ACT TGG       1074
Tyr Asp His Pro Asp Val Ala Ala Glu Ile Lys Arg Trp Gly Thr Trp
        205                 210                 215

TAT GCC AAT GAA CTG CAA TTG GAC GGT TTC CGT CTT GAT GCT GTC AAA       1122
Tyr Ala Asn Glu Leu Gln Leu Asp Gly Phe Arg Leu Asp Ala Val Lys
    220                 225                 230

CAC ATT AAA TTT TCT TTT TTG CGG GAT TGG GTT AAT CAT GTC AGG GAA       1170
His Ile Lys Phe Ser Phe Leu Arg Asp Trp Val Asn His Val Arg Glu
235                 240                 245                 250

AAA ACG GGG AAG GAA ATG TTT ACG GTA GCT GAA TAT TGG CAG AAT GAC       1218
Lys Thr Gly Lys Glu Met Phe Thr Val Ala Glu Tyr Trp Gln Asn Asp
                255                 260                 265

TTG GGC GCG CTG GAA AAC TAT TTG AAC AAA ACA AAT TTT AAT CAT TCA       1266
Leu Gly Ala Leu Glu Asn Tyr Leu Asn Lys Thr Asn Phe Asn His Ser
            270                 275                 280

GTG TTT GAC GTG CCG CTT CAT TAT CAG TTC CAT GCT GCA TCG ACA CAG       1314
Val Phe Asp Val Pro Leu His Tyr Gln Phe His Ala Ala Ser Thr Gln
        285                 290                 295

GGA GGC GGC TAT GAT ATG AGG AAA TTG CTG AAC GGT ACG GTC GTT TCC       1362
Gly Gly Gly Tyr Asp Met Arg Lys Leu Leu Asn Gly Thr Val Val Ser
    300                 305                 310

AAG CAT CCG TTG AAA TCG GTT ACA TTT GTC GAT AAC CAT GAT ACA CAG       1410
Lys His Pro Leu Lys Ser Val Thr Phe Val Asp Asn His Asp Thr Gln
315                 320                 325                 330

CCG GGG CAA TCG CTT GAG TCG ACT GTC CAA ACA TGG TTT AAG CCG CTT       1458
Pro Gly Gln Ser Leu Glu Ser Thr Val Gln Thr Trp Phe Lys Pro Leu
                335                 340                 345

GCT TAC GCT TTT ATT CTC ACA AGG GAA TCT GGA TAC CCT CAG GTT TTC       1506
Ala Tyr Ala Phe Ile Leu Thr Arg Glu Ser Gly Tyr Pro Gln Val Phe
            350                 355                 360

TAC GGG GAT ATG TAC GGG ACG AAA GGA GAC TCC CAG CGC GAA ATT CCT       1554
Tyr Gly Asp Met Tyr Gly Thr Lys Gly Asp Ser Gln Arg Glu Ile Pro
        365                 370                 375

GCC TTG AAA CAC AAA ATT GAA CCG ATC TTA AAA GCG AGA AAA CAG TAT       1602
Ala Leu Lys His Lys Ile Glu Pro Ile Leu Lys Ala Arg Lys Gln Tyr
    380                 385                 390

GCG TAC GGA GCA CAG CAT GAT TAT TTC GAC CAC CAT GAC ATT GTC GGC       1650
Ala Tyr Gly Ala Gln His Asp Tyr Phe Asp His His Asp Ile Val Gly
395                 400                 405                 410

TGG ACA AGG GAA GGC GAC AGC TCG GTT GCA AAT TCA GGT TTG GCG GCA       1698
Trp Thr Arg Glu Gly Asp Ser Ser Val Ala Asn Ser Gly Leu Ala Ala
                415                 420                 425

TTA ATA ACA GAC GGA CCC GGT GGG GCA AAG CGA ATG TAT GTC GGC CGG       1746
Leu Ile Thr Asp Gly Pro Gly Gly Ala Lys Arg Met Tyr Val Gly Arg
            430                 435                 440

CAA AAC GCC GGT GAG ACA TGG CAT GAC ATT ACC GGA AAC CGT TCG GAG       1794
Gln Asn Ala Gly Glu Thr Trp His Asp Ile Thr Gly Asn Arg Ser Glu
        445                 450                 455

CCG GTT GTC ATC AAT TCG GAA GGC TGG GGA GAG TTT CAC GTA AAC GGC       1842
Pro Val Val Ile Asn Ser Glu Gly Trp Gly Glu Phe His Val Asn Gly
    460                 465                 470

GGG TCG GTT TCA ATT TAT GTT CAA AGA TAG AAGAGCAGAG AGGACGGATT         1892
Gly Ser Val Ser Ile Tyr Val Gln Arg
```

-continued 4 7 5 4 8 0

TCCTGAAGGA AATCCGTTTT TTTATTTT 1920

( 2 ) INFORMATION FOR SEQ ID NO:2:

( i ) SEQUENCE CHARACTERISTICS:
( A ) LENGTH: 512 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Lys Gln Gln Lys Arg Leu Tyr Ala Arg Leu Leu Thr Leu Leu Phe
-29         -25             -20                 -15

Ala Leu Ile Phe Leu Leu Pro His Ser Ala Ala Ala Ala Ala Asn Leu
            -10                 -5                  1

Asn Gly Thr Leu Met Gln Tyr Phe Glu Trp Tyr Met Pro Asn Asp Gly
     5                  10                  15

Gln His Trp Arg Arg Leu Gln Asn Asp Ser Ala Tyr Leu Ala Glu His
 20                  25                  30                  35

Gly Ile Thr Ala Val Trp Ile Pro Pro Ala Tyr Lys Gly Thr Ser Gln
                 40                  45                  50

Ala Asp Val Gly Tyr Gly Ala Tyr Asp Leu Tyr Asp Leu Gly Glu Phe
             55                  60                  65

His Gln Lys Gly Thr Val Arg Thr Lys Tyr Gly Thr Lys Gly Glu Leu
         70                  75                  80

Gln Ser Ala Ile Lys Ser Leu His Ser Arg Asp Ile Asn Val Tyr Gly
     85                  90                  95

Asp Val Val Ile Asn His Lys Gly Gly Ala Asp Ala Thr Glu Asp Val
100                 105                 110                 115

Thr Ala Val Glu Val Asp Pro Ala Asp Arg Asn Arg Val Ile Ser Gly
                120                 125                 130

Glu His Leu Ile Lys Ala Trp Thr His Phe His Phe Pro Gly Arg Gly
            135                 140                 145

Ser Thr Tyr Ser Asp Phe Lys Trp His Trp Tyr His Phe Asp Gly Thr
        150                 155                 160

Asp Trp Asp Glu Ser Arg Lys Leu Asn Arg Ile Tyr Lys Phe Gln Gly
    165                 170                 175

Lys Ala Trp Asp Trp Glu Val Ser Asn Glu Asn Gly Asn Tyr Asp Tyr
180                 185                 190                 195

Leu Met Tyr Ala Asp Ile Asp Tyr Asp His Pro Asp Val Ala Ala Glu
                200                 205                 210

Ile Lys Arg Trp Gly Thr Trp Tyr Ala Asn Glu Leu Gln Leu Asp Gly
            215                 220                 225

Phe Arg Leu Asp Ala Val Lys His Ile Lys Phe Ser Phe Leu Arg Asp
        230                 235                 240

Trp Val Asn His Val Arg Glu Lys Thr Gly Lys Glu Met Phe Thr Val
    245                 250                 255

Ala Glu Tyr Trp Gln Asn Asp Leu Gly Ala Leu Glu Asn Tyr Leu Asn
260                 265                 270                 275

Lys Thr Asn Phe Asn His Ser Val Phe Asp Val Pro Leu His Tyr Gln
                280                 285                 290

Phe His Ala Ala Ser Thr Gln Gly Gly Gly Tyr Asp Met Arg Lys Leu
            295                 300                 305

Leu Asn Gly Thr Val Val Ser Lys His Pro Leu Lys Ser Val Thr Phe
```

310 315 320
Val Asp Asn His Asp Thr Gln Pro Gly Gln Ser Leu Glu Ser Thr Val
325 330 335
Gln Thr Trp Phe Lys Pro Leu Ala Tyr Ala Phe Ile Leu Thr Arg Glu
340 345 350 355
Ser Gly Tyr Pro Gln Val Phe Tyr Gly Asp Met Tyr Gly Thr Lys Gly
360 365 370
Asp Ser Gln Arg Glu Ile Pro Ala Leu Lys His Lys Ile Glu Pro Ile
375 380 385
Leu Lys Ala Arg Lys Gln Tyr Ala Tyr Gly Ala Gln His Asp Tyr Phe
390 395 400
Asp His His Asp Ile Val Gly Trp Thr Arg Glu Gly Asp Ser Ser Val
405 410 415
Ala Asn Ser Gly Leu Ala Ala Leu Ile Thr Asp Gly Pro Gly Gly Ala
420 425 430 435
Lys Arg Met Tyr Val Gly Arg Gln Asn Ala Gly Glu Thr Trp His Asp
440 445 450
Ile Thr Gly Asn Arg Ser Glu Pro Val Val Ile Asn Ser Glu Gly Trp
455 460 465
Gly Glu Phe His Val Asn Gly Gly Ser Val Ser Ile Tyr Val Gln Arg
470 475 480

( 2 ) INFORMATION FOR SEQ ID NO:3:

( i ) SEQUENCE CHARACTERISTICS:
( A ) LENGTH: 2084 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 250..1794

( i x ) FEATURE:
( A ) NAME/KEY: sig_peptide
( B ) LOCATION: 250..342

( i x ) FEATURE:
( A ) NAME/KEY: mat_peptide
( B ) LOCATION: 343..1791

( x i ) SEQUENCE DESCRIPTION: SEQ ID NO:3:

GCCCCGCACA TACGAAAAGA CTGGCTGAAA ACATTGAGCC TTTGATGACT GATGATTTGG 60

CTGAAGAAGT GGATCGATTG TTTGAGAAAA GAAGAAGACC ATAAAAATAC CTTGTCTGTC 120

ATCAGACAGG GTATTTTTTA TGCTGTCCAG ACTGTCCGCT GTGTAAAAAT AAGGAATAAA 180

GGGGGGTTGT TATTATTTTA CTGATATGTA AAATATAATT TGTATAAGAA AATGAGAGGG 240

AGAGGAAAC ATG ATT CAA AAA CGA AAG CGG ACA GTT TCG TTC AGA CTT 288
Met Ile Gln Lys Arg Lys Arg Thr Val Ser Phe Arg Leu
-31 -30 -25 -20

GTG CTT ATG TGC ACG CTG TTA TTT GTC AGT TTG CCG ATT ACA AAA ACA 336
Val Leu Met Cys Thr Leu Leu Phe Val Ser Leu Pro Ile Thr Lys Thr
-15 -10 -5

TCA GCC GTA AAT GGC ACG CTG ATG CAG TAT TTT GAA TGG TAT ACG CCG 384
Ser Ala Val Asn Gly Thr Leu Met Gln Tyr Phe Glu Trp Tyr Thr Pro
1 5 10

AAC GAC GGC CAG CAT TGG AAA CGA TTG CAG AAT GAT GCG GAA CAT TTA 432
Asn Asp Gly Gln His Trp Lys Arg Leu Gln Asn Asp Ala Glu His Leu
15 20 25 30

TCG GAT ATC GGA ATC ACT GCC GTC TGG ATT CCT CCC GCA TAC AAA GGA 480

-continued

```
Ser Asp Ile Gly Ile Thr Ala Val Trp Ile Pro Pro Ala Tyr Lys Gly
                35                  40                  45

TTG AGC CAA TCC GAT AAC GGA TAC GGA CCT TAT GAT TTG TAT GAT TTA      528
Leu Ser Gln Ser Asp Asn Gly Tyr Gly Pro Tyr Asp Leu Tyr Asp Leu
            50                  55                  60

GGA GAA TTC CAG CAA AAA GGG ACG GTC AGA ACG AAA TAC GGC ACA AAA      576
Gly Glu Phe Gln Gln Lys Gly Thr Val Arg Thr Lys Tyr Gly Thr Lys
        65                  70                  75

TCA GAG CTT CAA GAT GCG ATC GGC TCA CTG CAT TCC CGG AAC GTC CAA      624
Ser Glu Leu Gln Asp Ala Ile Gly Ser Leu His Ser Arg Asn Val Gln
    80                  85                  90

GTA TAC GGA GAT GTG GTT TTG AAT CAT AAG GCT GGT GCT GAT GCA ACA      672
Val Tyr Gly Asp Val Val Leu Asn His Lys Ala Gly Ala Asp Ala Thr
95                  100                 105                 110

GAA GAT GTA ACT GCC GTC GAA GTC AAT CCG GCC AAT AGA AAT CAG GAA      720
Glu Asp Val Thr Ala Val Glu Val Asn Pro Ala Asn Arg Asn Gln Glu
                115                 120                 125

ACT TCG GAG GAA TAT CAA ATC AAA GCG TGG ACG GAT TTT CGT TTT CCG      768
Thr Ser Glu Glu Tyr Gln Ile Lys Ala Trp Thr Asp Phe Arg Phe Pro
            130                 135                 140

GGC CGT GGA AAC ACG TAC AGT GAT TTT AAA TGG CAT TGG TAT CAT TTC      816
Gly Arg Gly Asn Thr Tyr Ser Asp Phe Lys Trp His Trp Tyr His Phe
        145                 150                 155

GAC GGA GCG GAC TGG GAT GAA TCC CGG AAG ATC AGC CGC ATC TTT AAG      864
Asp Gly Ala Asp Trp Asp Glu Ser Arg Lys Ile Ser Arg Ile Phe Lys
    160                 165                 170

TTT CGT GGG GAA GGA AAA GCG TGG GAT TGG GAA GTA TCA AGT GAA AAC      912
Phe Arg Gly Glu Gly Lys Ala Trp Asp Trp Glu Val Ser Ser Glu Asn
175                 180                 185                 190

GGC AAC TAT GAC TAT TTA ATG TAT GCT GAT GTT GAC TAC GAC CAC CCT      960
Gly Asn Tyr Asp Tyr Leu Met Tyr Ala Asp Val Asp Tyr Asp His Pro
                195                 200                 205

GAT GTC GTG GCA GAG ACA AAA AAA TGG GGT ATC TGG TAT GCG AAT GAA     1008
Asp Val Val Ala Glu Thr Lys Lys Trp Gly Ile Trp Tyr Ala Asn Glu
            210                 215                 220

CTG TCA TTA GAC GGC TTC CGT ATT GAT GCC GCC AAA CAT ATT AAA TTT     1056
Leu Ser Leu Asp Gly Phe Arg Ile Asp Ala Ala Lys His Ile Lys Phe
        225                 230                 235

TCA TTT CTG CGT GAT TGG GTT CAG GCG GTC AGA CAG GCG ACG GGA AAA     1104
Ser Phe Leu Arg Asp Trp Val Gln Ala Val Arg Gln Ala Thr Gly Lys
    240                 245                 250

GAA ATG TTT ACG GTT GCG GAG TAT TGG CAG AAT AAT GCC GGG AAA CTC     1152
Glu Met Phe Thr Val Ala Glu Tyr Trp Gln Asn Asn Ala Gly Lys Leu
255                 260                 265                 270

GAA AAC TAC TTG AAT AAA ACA AGC TTT AAT CAA TCC GTG TTT GAT GTT     1200
Glu Asn Tyr Leu Asn Lys Thr Ser Phe Asn Gln Ser Val Phe Asp Val
                275                 280                 285

CCG CTT CAT TTC AAT TTA CAG GCG GCT TCC TCA CAA GGA GGC GGA TAT     1248
Pro Leu His Phe Asn Leu Gln Ala Ala Ser Ser Gln Gly Gly Gly Tyr
            290                 295                 300

GAT ATG AGG CGT TTG CTG GAC GGT ACC GTT GTG TCC AGG CAT CCG GAA     1296
Asp Met Arg Arg Leu Leu Asp Gly Thr Val Val Ser Arg His Pro Glu
        305                 310                 315

AAG GCG GTT ACA TTT GTT GAA AAT CAT GAC ACA CAG CCG GGA CAG TCA     1344
Lys Ala Val Thr Phe Val Glu Asn His Asp Thr Gln Pro Gly Gln Ser
    320                 325                 330

TTG GAA TCG ACA GTC CAA ACT TGG TTT AAA CCG CTT GCA TAC GCC TTT     1392
Leu Glu Ser Thr Val Gln Thr Trp Phe Lys Pro Leu Ala Tyr Ala Phe
335                 340                 345                 350

ATT TTG ACA AGA GAA TCC GGT TAT CCT CAG GTG TTC TAT GGG GAT ATG     1440
```

-continued

```
Ile Leu Thr Arg Glu Ser Gly Tyr Pro Gln Val Phe Tyr Gly Asp Met
                355                 360                 365

TAC GGG ACA AAA GGG ACA TCG CCA AAG GAA ATT CCC TCA CTG AAA GAT     1488
Tyr Gly Thr Lys Gly Thr Ser Pro Lys Glu Ile Pro Ser Leu Lys Asp
            370                 375                 380

AAT ATA GAG CCG ATT TTA AAA GCG CGT AAG GAG TAC GCA TAC GGG CCC     1536
Asn Ile Glu Pro Ile Leu Lys Ala Arg Lys Glu Tyr Ala Tyr Gly Pro
        385                 390                 395

CAG CAC GAT TAT ATT GAC CAC CCG GAT GTG ATC GGA TGG ACG AGG GAA     1584
Gln His Asp Tyr Ile Asp His Pro Asp Val Ile Gly Trp Thr Arg Glu
    400                 405                 410

GGT GAC AGC TCC GCC GCC AAA TCA GGT TTG GCC GCT TTA ATC ACG GAC     1632
Gly Asp Ser Ser Ala Ala Lys Ser Gly Leu Ala Ala Leu Ile Thr Asp
415                 420                 425                 430

GGA CCC GGC GGA TCA AAG CGG ATG TAT GCC GGC CTG AAA AAT GCC GGC     1680
Gly Pro Gly Gly Ser Lys Arg Met Tyr Ala Gly Leu Lys Asn Ala Gly
                435                 440                 445

GAG ACA TGG TAT GAC ATA ACG GGC AAC CGT TCA GAT ACT GTA AAA ATC     1728
Glu Thr Trp Tyr Asp Ile Thr Gly Asn Arg Ser Asp Thr Val Lys Ile
            450                 455                 460

GGA TCT GAC GGC TGG GGA GAG TTT CAT GTA AAC GAT GGG TCC GTC TCC     1776
Gly Ser Asp Gly Trp Gly Glu Phe His Val Asn Asp Gly Ser Val Ser
        465                 470                 475

ATT TAT GTT CAG AAA TAA GGTAATAAAA AAACACCTCC AAGCTGAGTG            1824
Ile Tyr Val Gln Lys
    480

CGGGTATCAG CTTGGAGGTG CGTTTATTTT TTCAGCCGTA TGACAAGGTC GGCATCAGGT   1884

GTGACAAATA CGGTATGCTG GCTGTCATAG GTGACAAATC CGGGTTTTGC GCCGTTTGGC   1944

TTTTTCACAT GTCTGATTTT TGTATAATCA ACAGGCACGG AGCCGGAATC TTTCGCCTTG   2004

GAAAAATAAG CGGCGATCGT AGCTGCTTCC AATATGGATT GTTCATCGGG ATCGCTGCTT   2064

TTAATCACAA CGTGGGATCC                                               2084
```

( 2 ) INFORMATION FOR SEQ ID NO:4:

( i ) SEQUENCE CHARACTERISTICS:
( A ) LENGTH: 514 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Ile Gln Lys Arg Lys Arg Thr Val Ser Phe Arg Leu Val Leu Met
-31 -30                 -25                 -20

Cys Thr Leu Leu Phe Val Ser Leu Pro Ile Thr Lys Thr Ser Ala Val
-15                 -10                  -5                   1

Asn Gly Thr Leu Met Gln Tyr Phe Glu Trp Tyr Thr Pro Asn Asp Gly
              5                  10                  15

Gln His Trp Lys Arg Leu Gln Asn Asp Ala Glu His Leu Ser Asp Ile
         20                  25                  30

Gly Ile Thr Ala Val Trp Ile Pro Pro Ala Tyr Lys Gly Leu Ser Gln
     35                  40                  45

Ser Asp Asn Gly Tyr Gly Pro Tyr Asp Leu Tyr Asp Leu Gly Glu Phe
 50                  55                  60                  65

Gln Gln Lys Gly Thr Val Arg Thr Lys Tyr Gly Thr Lys Ser Glu Leu
                 70                  75                  80

Gln Asp Ala Ile Gly Ser Leu His Ser Arg Asn Val Gln Val Tyr Gly
              85                  90                  95
```

-continued

Asp Val Val Leu Asn His Lys Ala Gly Ala Asp Ala Thr Glu Asp Val
100 105 110

Thr Ala Val Glu Val Asn Pro Ala Asn Arg Asn Gln Glu Thr Ser Glu
115 120 125

Glu Tyr Gln Ile Lys Ala Trp Thr Asp Phe Arg Phe Pro Gly Arg Gly
130 135 140 145

Asn Thr Tyr Ser Asp Phe Lys Trp His Trp Tyr His Phe Asp Gly Ala
150 155 160

Asp Trp Asp Glu Ser Arg Lys Ile Ser Arg Ile Phe Lys Phe Arg Gly
165 170 175

Glu Gly Lys Ala Trp Asp Trp Glu Val Ser Ser Glu Asn Gly Asn Tyr
180 185 190

Asp Tyr Leu Met Tyr Ala Asp Val Asp Tyr Asp His Pro Asp Val Val
195 200 205

Ala Glu Thr Lys Lys Trp Gly Ile Trp Tyr Ala Asn Glu Leu Ser Leu
210 215 220 225

Asp Gly Phe Arg Ile Asp Ala Ala Lys His Ile Lys Phe Ser Phe Leu
230 235 240

Arg Asp Trp Val Gln Ala Val Arg Gln Ala Thr Gly Lys Glu Met Phe
245 250 255

Thr Val Ala Glu Tyr Trp Gln Asn Asn Ala Gly Lys Leu Glu Asn Tyr
260 265 270

Leu Asn Lys Thr Ser Phe Asn Gln Ser Val Phe Asp Val Pro Leu His
275 280 285

Phe Asn Leu Gln Ala Ala Ser Ser Gln Gly Gly Gly Tyr Asp Met Arg
290 295 300 305

Arg Leu Leu Asp Gly Thr Val Val Ser Arg His Pro Glu Lys Ala Val
310 315 320

Thr Phe Val Glu Asn His Asp Thr Gln Pro Gly Gln Ser Leu Glu Ser
325 330 335

Thr Val Gln Thr Trp Phe Lys Pro Leu Ala Tyr Ala Phe Ile Leu Thr
340 345 350

Arg Glu Ser Gly Tyr Pro Gln Val Phe Tyr Gly Asp Met Tyr Gly Thr
355 360 365

Lys Gly Thr Ser Pro Lys Glu Ile Pro Ser Leu Lys Asp Asn Ile Glu
370 375 380 385

Pro Ile Leu Lys Ala Arg Lys Glu Tyr Ala Tyr Gly Pro Gln His Asp
390 395 400

Tyr Ile Asp His Pro Asp Val Ile Gly Trp Thr Arg Glu Gly Asp Ser
405 410 415

Ser Ala Ala Lys Ser Gly Leu Ala Ala Leu Ile Thr Asp Gly Pro Gly
420 425 430

Gly Ser Lys Arg Met Tyr Ala Gly Leu Lys Asn Ala Gly Glu Thr Trp
435 440 445

Tyr Asp Ile Thr Gly Asn Arg Ser Asp Thr Val Lys Ile Gly Ser Asp
450 455 460 465

Gly Trp Gly Glu Phe His Val Asn Asp Gly Ser Val Ser Ile Tyr Val
470 475 480

Gln Lys ( 2 ) INFORMATION FOR SEQ ID NO:5:

( i ) SEQUENCE CHARACTERISTICS:

( A ) LENGTH: 1814 base pairs ( B ) TYPE: nucleic acid
( C ) STRANDEDNESS: single
( D ) TOPOLOGY: linear ( i x ) FEATURE:
( A ) NAME/KEY: CDS
( B ) LOCATION: 156..1805

( i x ) FEATURE:
( A ) NAME/KEY: sig_peptide
( B ) LOCATION: 156..257

( i x ) FEATURE:
( A ) NAME/KEY: mat_peptide
( B ) LOCATION: 258..1802

( x i ) SEQUENCE DESCRIPTION: SEQ ID NO:5:

```
AAATTCGATA TTGAAAACGA TTACAAATAA AAATTATAAT AGACGTAAAC GTTCGAGGGT      60

TTGCTCCCTT TTTACTCTTT TTATGCAATC GTTTCCCTTA ATTTTTTGGA AGCCAAACCG     120

TCGAATGTAA CATTTGATTA AGGGGGAAGG GCATT GTG CTA ACG TTT CAC CGC        173
                                       Val Leu Thr Phe His Arg
                                       -34                 -30

ATC ATT CGA AAA GGA TGG ATG TTC CTG CTC GCG TTT TTG CTC ACT GTC       221
Ile Ile Arg Lys Gly Trp Met Phe Leu Leu Ala Phe Leu Leu Thr Val
            -25                 -20                 -15

TCG CTG TTC TGC CCA ACA GGA CAG CCC GCC AAG GCT GCC GCA CCG TTT       269
Ser Leu Phe Cys Pro Thr Gly Gln Pro Ala Lys Ala Ala Ala Pro Phe
        -10                 -5                  1

AAC GGC ACC ATG ATG CAG TAT TTT GAA TGG TAC TTG CCG GAT GAT GGC       317
Asn Gly Thr Met Met Gln Tyr Phe Glu Trp Tyr Leu Pro Asp Asp Gly
  5                  10                  15                  20

ACG TTA TGG ACC AAA GTG GCC AAT GAA GCC AAC AAC TTA TCC AGC CTT       365
Thr Leu Trp Thr Lys Val Ala Asn Glu Ala Asn Asn Leu Ser Ser Leu
                 25                  30                  35

GGC ATC ACC GCT CTT TGG CTG CCG CCC GCT TAC AAA GGA ACA AGC CGC       413
Gly Ile Thr Ala Leu Trp Leu Pro Pro Ala Tyr Lys Gly Thr Ser Arg
             40                  45                  50

AGC GAC GTA GGG TAC GGA GTA TAC GAC TTG TAT GAC CTC GGC GAA TTC       461
Ser Asp Val Gly Tyr Gly Val Tyr Asp Leu Tyr Asp Leu Gly Glu Phe
         55                  60                  65

AAT CAA AAA GGG ACC GTC CGC ACA AAA TAC GGA ACA AAA GCT CAA TAT       509
Asn Gln Lys Gly Thr Val Arg Thr Lys Tyr Gly Thr Lys Ala Gln Tyr
     70                  75                  80

CTT CAA GCC ATT CAA GCC GCC CAC GCC GCT GGA ATG CAA GTG TAC GCC       557
Leu Gln Ala Ile Gln Ala Ala His Ala Ala Gly Met Gln Val Tyr Ala
 85                  90                  95                 100

GAT GTC GTG TTC GAC CAT AAA GGC GGC GCT GAC GGC ACG GAA TGG GTG       605
Asp Val Val Phe Asp His Lys Gly Gly Ala Asp Gly Thr Glu Trp Val
                105                 110                 115

GAC GCC GTC GAA GTC AAT CCG TCC GAC CGC AAC CAA GAA ATC TCG GGC       653
Asp Ala Val Glu Val Asn Pro Ser Asp Arg Asn Gln Glu Ile Ser Gly
            120                 125                 130

ACC TAT CAA ATC CAA GCA TGG ACG AAA TTT GAT TTT CCC GGG CGG GGC       701
Thr Tyr Gln Ile Gln Ala Trp Thr Lys Phe Asp Phe Pro Gly Arg Gly
        135                 140                 145

AAC ACC TAC TCC AGC TTT AAG TGG CGC TGG TAC CAT TTT GAC GGC GTT       749
Asn Thr Tyr Ser Ser Phe Lys Trp Arg Trp Tyr His Phe Asp Gly Val
    150                 155                 160

GAT TGG GAC GAA AGC CGA AAA TTG AGC CGC ATT TAC AAA TTC CGC GGC       797
Asp Trp Asp Glu Ser Arg Lys Leu Ser Arg Ile Tyr Lys Phe Arg Gly
165                 170                 175                 180

ATC GGC AAA GCG TGG GAT TGG GAA GTA GAC ACG GAA AAC GGA AAC TAT       845
Ile Gly Lys Ala Trp Asp Trp Glu Val Asp Thr Glu Asn Gly Asn Tyr
```

-continued

```
                            185                        190                        195

GAC TAC TTA ATG TAT GCC GAC CTT GAT ATG GAT CAT CCC GAA GTC GTG     893
Asp Tyr Leu Met Tyr Ala Asp Leu Asp Met Asp His Pro Glu Val Val
            200                     205                     210

ACC GAG CTG AAA AAC TGG GGG AAA TGG TAT GTC AAC ACA ACG AAC ATT     941
Thr Glu Leu Lys Asn Trp Gly Lys Trp Tyr Val Asn Thr Thr Asn Ile
        215                     220                     225

GAT GGG TTC CGG CTT GAT GCC GTC AAG CAT ATT AAG TTC AGT TTT TTT     989
Asp Gly Phe Arg Leu Asp Ala Val Lys His Ile Lys Phe Ser Phe Phe
    230                     235                     240

CCT GAT TGG TTG TCG TAT GTG CGT TCT CAG ACT GGC AAG CCG CTA TTT    1037
Pro Asp Trp Leu Ser Tyr Val Arg Ser Gln Thr Gly Lys Pro Leu Phe
245                 250                     255                 260

ACC GTC GGG GAA TAT TGG AGC TAT GAC ATC AAC AAG TTG CAC AAT TAC    1085
Thr Val Gly Glu Tyr Trp Ser Tyr Asp Ile Asn Lys Leu His Asn Tyr
                265                     270                     275

ATT ACG AAA ACA GAC GGA ACG ATG TCT TTG TTT GAT GCC CCG TTA CAC    1133
Ile Thr Lys Thr Asp Gly Thr Met Ser Leu Phe Asp Ala Pro Leu His
            280                     285                     290

AAC AAA TTT TAT ACC GCT TCC AAA TCA GGG GGC GCA TTT GAT ATG CGC    1181
Asn Lys Phe Tyr Thr Ala Ser Lys Ser Gly Gly Ala Phe Asp Met Arg
        295                     300                     305

ACG TTA ATG ACC AAT ACT CTC ATG AAA GAT CAA CCG ACA TTG GCC GTC    1229
Thr Leu Met Thr Asn Thr Leu Met Lys Asp Gln Pro Thr Leu Ala Val
    310                     315                     320

ACC TTC GTT GAT AAT CAT GAC ACC GAA CCC GGC CAA GCG CTG CAG TCA    1277
Thr Phe Val Asp Asn His Asp Thr Glu Pro Gly Gln Ala Leu Gln Ser
325                 330                     335                 340

TGG GTC GAC CCA TGG TTC AAA CCG TTG GCT TAC GCC TTT ATT CTA ACT    1325
Trp Val Asp Pro Trp Phe Lys Pro Leu Ala Tyr Ala Phe Ile Leu Thr
                345                     350                     355

CGG CAG GAA GGA TAC CCG TGC GTC TTT TAT GGT GAC TAT TAT GGC ATT    1373
Arg Gln Glu Gly Tyr Pro Cys Val Phe Tyr Gly Asp Tyr Tyr Gly Ile
            360                     365                     370

CCA CAA TAT AAC ATT CCT TCG CTG AAA AGC AAA ATC GAT CCG CTC CTC    1421
Pro Gln Tyr Asn Ile Pro Ser Leu Lys Ser Lys Ile Asp Pro Leu Leu
        375                     380                     385

ATC GCG CGC AGG GAT TAT GCT TAC GGA ACG CAA CAT GAT TAT CTT GAT    1469
Ile Ala Arg Arg Asp Tyr Ala Tyr Gly Thr Gln His Asp Tyr Leu Asp
    390                     395                     400

CAC TCC GAC ATC ATC GGG TGG ACA AGG GAA GGG GGC ACT GAA AAA CCA    1517
His Ser Asp Ile Ile Gly Trp Thr Arg Glu Gly Gly Thr Glu Lys Pro
405                 410                     415                 420

GGA TCC GGA CTG GCC GCA CTG ATC ACC GAT GGG CCG GGA GGA AGC AAA    1565
Gly Ser Gly Leu Ala Ala Leu Ile Thr Asp Gly Pro Gly Gly Ser Lys
                425                     430                     435

TGG ATG TAC GTT GGC AAA CAA CAC GCT GGA AAA GTG TTC TAT GAC CTT    1613
Trp Met Tyr Val Gly Lys Gln His Ala Gly Lys Val Phe Tyr Asp Leu
            440                     445                     450

ACC GGC AAC CGG AGT GAC ACC GTC ACC ATC AAC AGT GAT GGA TGG GGG    1661
Thr Gly Asn Arg Ser Asp Thr Val Thr Ile Asn Ser Asp Gly Trp Gly
        455                     460                     465

GAA TTC AAA GTC AAT GGC GGT TCG GTT TCG GTT TGG GTT CCT AGA AAA    1709
Glu Phe Lys Val Asn Gly Gly Ser Val Ser Val Trp Val Pro Arg Lys
    470                     475                     480

ACG ACC GTT TCT ACC ATC GCT CGG CCG ATC ACA ACC CGA CCG TGG ACT    1757
Thr Thr Val Ser Thr Ile Ala Arg Pro Ile Thr Thr Arg Pro Trp Thr
485                 490                     495                 500

GGT GAA TTC GTC CGT TGG ACC GAA CCA CGG TTG GTG GCA TGG CCT TGA    1805
Gly Glu Phe Val Arg Trp Thr Glu Pro Arg Leu Val Ala Trp Pro
```

-continued 505 510 515

TGCCTGCGA 1814

( 2 ) INFORMATION FOR SEQ ID NO:6:

( i ) SEQUENCE CHARACTERISTICS:
( A ) LENGTH: 549 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Val Leu Thr Phe His Arg Ile Ile Arg Lys Gly Trp Met Phe Leu Leu
-34             -30                 -25                 -20

Ala Phe Leu Leu Thr Val Ser Leu Phe Cys Pro Thr Gly Gln Pro Ala
            -15                 -10                 -5

Lys Ala Ala Ala Pro Phe Asn Gly Thr Met Met Gln Tyr Phe Glu Trp
         1                   5                  10

Tyr Leu Pro Asp Asp Gly Thr Leu Trp Thr Lys Val Ala Asn Glu Ala
 15                  20                  25                  30

Asn Asn Leu Ser Ser Leu Gly Ile Thr Ala Leu Trp Leu Pro Pro Ala
                 35                  40                  45

Tyr Lys Gly Thr Ser Arg Ser Asp Val Gly Tyr Gly Val Tyr Asp Leu
             50                  55                  60

Tyr Asp Leu Gly Glu Phe Asn Gln Lys Gly Thr Val Arg Thr Lys Tyr
         65                  70                  75

Gly Thr Lys Ala Gln Tyr Leu Gln Ala Ile Gln Ala Ala His Ala Ala
     80                  85                  90

Gly Met Gln Val Tyr Ala Asp Val Val Phe Asp His Lys Gly Gly Ala
 95                 100                 105                 110

Asp Gly Thr Glu Trp Val Asp Ala Val Glu Val Asn Pro Ser Asp Arg
                115                 120                 125

Asn Gln Glu Ile Ser Gly Thr Tyr Gln Ile Gln Ala Trp Thr Lys Phe
            130                 135                 140

Asp Phe Pro Gly Arg Gly Asn Thr Tyr Ser Ser Phe Lys Trp Arg Trp
        145                 150                 155

Tyr His Phe Asp Gly Val Asp Trp Asp Glu Ser Arg Lys Leu Ser Arg
    160                 165                 170

Ile Tyr Lys Phe Arg Gly Ile Gly Lys Ala Trp Asp Trp Glu Val Asp
175                 180                 185                 190

Thr Glu Asn Gly Asn Tyr Asp Tyr Leu Met Tyr Ala Asp Leu Asp Met
                195                 200                 205

Asp His Pro Glu Val Val Thr Glu Leu Lys Asn Trp Gly Lys Trp Tyr
            210                 215                 220

Val Asn Thr Thr Asn Ile Asp Gly Phe Arg Leu Asp Ala Val Lys His
        225                 230                 235

Ile Lys Phe Ser Phe Phe Pro Asp Trp Leu Ser Tyr Val Arg Ser Gln
    240                 245                 250

Thr Gly Lys Pro Leu Phe Thr Val Gly Glu Tyr Trp Ser Tyr Asp Ile
255                 260                 265                 270

Asn Lys Leu His Asn Tyr Ile Thr Lys Thr Asp Gly Thr Met Ser Leu
                275                 280                 285

Phe Asp Ala Pro Leu His Asn Lys Phe Tyr Thr Ala Ser Lys Ser Gly
            290                 295                 300

Gly Ala Phe Asp Met Arg Thr Leu Met Thr Asn Thr Leu Met Lys Asp
```

305 310 315

Gln Pro Thr Leu Ala Val Thr Phe Val Asp Asn His Asp Thr Glu Pro
320 325 330

Gly Gln Ala Leu Gln Ser Trp Val Asp Pro Trp Phe Lys Pro Leu Ala
335 340 345 350

Tyr Ala Phe Ile Leu Thr Arg Gln Glu Gly Tyr Pro Cys Val Phe Tyr
355 360 365

Gly Asp Tyr Tyr Gly Ile Pro Gln Tyr Asn Ile Pro Ser Leu Lys Ser
370 375 380

Lys Ile Asp Pro Leu Leu Ile Ala Arg Arg Asp Tyr Ala Tyr Gly Thr
385 390 395

Gln His Asp Tyr Leu Asp His Ser Asp Ile Ile Gly Trp Thr Arg Glu
400 405 410

Gly Gly Thr Glu Lys Pro Gly Ser Gly Leu Ala Ala Leu Ile Thr Asp
415 420 425 430

Gly Pro Gly Gly Ser Lys Trp Met Tyr Val Gly Lys Gln His Ala Gly
435 440 445

Lys Val Phe Tyr Asp Leu Thr Gly Asn Arg Ser Asp Thr Val Thr Ile
450 455 460

Asn Ser Asp Gly Trp Gly Glu Phe Lys Val Asn Gly Gly Ser Val Ser
465 470 475

Val Trp Val Pro Arg Lys Thr Thr Val Ser Thr Ile Ala Arg Pro Ile
480 485 490

Thr Thr Arg Pro Trp Thr Gly Glu Phe Val Arg Trp Thr Glu Pro Arg
495 500 505 510

Leu Val Ala Trp Pro
515

( 2 ) INFORMATION FOR SEQ ID NO:7:

( i ) SEQUENCE CHARACTERISTICS:
( A ) LENGTH: 478 amino acids
( B ) TYPE: amino acid
( C ) STRANDEDNESS: single
( D ) TOPOLOGY: linear ( x i ) SEQUENCE DESCRIPTION: SEQ ID NO:7:

Ala Thr Pro Ala Asp Trp Arg Ser Gln Ser Ile Tyr Phe Leu Leu Thr
1 5 10 15

Asp Arg Phe Ala Arg Thr Asp Gly Ser Thr Thr Ala Thr Cys Asn Thr
20 25 30

Ala Asp Gln Lys Tyr Cys Gly Gly Thr Trp Gln Gly Ile Ile Asp Lys
35 40 45

Leu Asp Tyr Ile Gln Gly Met Gly Phe Thr Ala Ile Trp Ile Thr Pro
50 55 60

Val Thr Ala Gln Leu Pro Gln Thr Thr Ala Tyr Gly Asp Ala Tyr His
65 70 75 80

Gly Tyr Trp Gln Gln Asp Ile Tyr Ser Leu Asn Glu Asn Tyr Gly Thr
85 90 95

Ala Asp Asp Leu Lys Ala Leu Ser Ser Ala Leu His Glu Arg Gly Met
100 105 110

Tyr Leu Met Val Asp Val Val Ala Asn His Met Gly Tyr Asp Gly Ala
115 120 125

Gly Ser Ser Val Asp Tyr Ser Val Phe Lys Pro Phe Ser Ser Gln Asp
130 135 140

Tyr Phe His Pro Phe Cys Phe Ile Gln Asn Tyr Glu Asp Gln Thr Gln

-continued 145 150 155 160

Val Glu Asp Cys Trp Leu Gly Asp Asn Thr Val Ser Leu Pro Asp Leu
165 170 175

Asp Thr Thr Lys Asp Val Val Lys Asn Glu Trp Tyr Asp Trp Val Gly
180 185 190

Ser Leu Val Ser Asn Tyr Ser Ile Asp Gly Leu Arg Ile Asp Thr Val
195 200 205

Lys His Val Gln Lys Asp Phe Trp Pro Gly Tyr Asn Lys Ala Ala Gly
210 215 220

Val Tyr Cys Ile Gly Glu Val Leu Asp Gly Asp Pro Ala Tyr Thr Cys
225 230 235 240

Pro Tyr Gln Asn Val Met Asp Gly Val Leu Asn Tyr Pro Ile Tyr Tyr
245 250 255

Pro Leu Leu Asn Ala Phe Lys Ser Thr Ser Gly Ser Met Asp Asp Leu
260 265 270

Tyr Asn Met Ile Asn Thr Val Lys Ser Asp Cys Pro Asp Ser Thr Leu
275 280 285

Leu Gly Thr Phe Val Glu Asn His Asp Asn Pro Arg Phe Ala Ser Tyr
290 295 300

Thr Asn Asp Ile Ala Leu Ala Lys Asn Val Ala Ala Phe Ile Ile Leu
305 310 315 320

Asn Asp Gly Ile Pro Ile Ile Tyr Ala Gly Gln Glu Gln His Tyr Ala
325 330 335

Gly Gly Asn Asp Pro Ala Asn Arg Glu Ala Thr Trp Leu Ser Gly Tyr
340 345 350

Pro Thr Asp Ser Glu Leu Tyr Lys Leu Ile Ala Ser Ala Asn Ala Ile
355 360 365

Arg Asn Tyr Ala Ile Ser Lys Asp Thr Gly Phe Val Thr Tyr Lys Asn
370 375 380

Trp Pro Ile Tyr Lys Asp Asp Ile Thr Ile Ala Met Arg Lys Gly Thr
385 390 395 400

Asp Gly Ser Gln Ile Val Thr Ile Leu Ser Asn Lys Gly Ala Ser Gly
405 410 415

Asp Ser Tyr Thr Leu Ser Leu Ser Gly Ala Gly Tyr Thr Ala Gly Gln
420 425 430

Gln Leu Thr Glu Val Ile Gly Cys Thr Thr Val Thr Val Gly Ser Asp
435 440 445

Gly Asn Val Pro Val Pro Met Ala Gly Gly Leu Pro Arg Val Leu Tyr
450 455 460

Pro Thr Glu Lys Leu Ala Gly Ser Lys Ile Cys Ser Ser Ser
465 470 475

( 2 ) INFORMATION FOR SEQ ID NO:8:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:8:

CACTTCAACG CACCTTTCAG C 21

( 2 ) INFORMATION FOR SEQ ID NO:9:

( i ) SEQUENCE CHARACTERISTICS:
( A ) LENGTH: 20 base pairs

-continued ( B ) TYPE: nucleic acid
( C ) STRANDEDNESS: single
( D ) TOPOLOGY: linear ( x i ) SEQUENCE DESCRIPTION: SEQ ID NO:9:

C A T G G A C T T C   A T T T A C T G G G   2 0

( 2 ) INFORMATION FOR SEQ ID NO:10:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:10:

C A C T G C C G T C   T G G A T T C C C C   2 0

( 2 ) INFORMATION FOR SEQ ID NO:11:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:11:

G G G A A T C C A G   A C G G C A G T G   1 9

( 2 ) INFORMATION FOR SEQ ID NO:12:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:12:

G A A T T C A A T C   A A A A A G G G A C   G G T T C G G   2 7

( 2 ) INFORMATION FOR SEQ ID NO:13:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:13:

C C G T C C C T T T   T T G A T T G A A T   T C G C C   2 5

( 2 ) INFORMATION FOR SEQ ID NO:14:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:14:

C G G C A T A C G T   C A A A T A A T C A   T A G T T G C   2 7

( 2 ) INFORMATION FOR SEQ ID NO:15:

( i ) SEQUENCE CHARACTERISTICS:
( A ) LENGTH: 43 base pairs
( B ) TYPE: nucleic acid
( C ) STRANDEDNESS: single -continued ( D ) TOPOLOGY: linear ( x i ) SEQUENCE DESCRIPTION: SEQ ID NO:15:

G G T A C T A T C G   T A A C A A T G G C   C G A T T G C T G A   C G C T G T T A T T   T G C   4 3

( 2 ) INFORMATION FOR SEQ ID NO:16:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:16:

G G G G T A C T A G   T A A C C C G G G C   C A T A C A G C G A   T T T T A A A T G G   4 0

( 2 ) INFORMATION FOR SEQ ID NO:17:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( x i ) SEQUENCE DESCRIPTION: SEQ ID NO:17:

G G G G T A C T A G   T A A C C C G G G C   C G G T T A C A T T   T G T C G A T A A C   C   4 1

( 2 ) INFORMATION FOR SEQ ID NO:18:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:18:

C T C G T C C C A A   T C G G T T C C G T   C   2 1

( 2 ) INFORMATION FOR SEQ ID NO:19:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:19:

G G C T T A A A C C   A T G T T T G G A C   2 0

( 2 ) INFORMATION FOR SEQ ID NO:20:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:20:

C A C T T C A A C G   C A C C T T T C A G   C   2 1

( 2 ) INFORMATION FOR SEQ ID NO:21:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear -continued ( x i ) SEQUENCE DESCRIPTION: SEQ ID NO:21:

CCTCATTCTG CAGCAGCGGC GGTTAATGGG ACGCTGATGC AG 42

( 2 ) INFORMATION FOR SEQ ID NO:22:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:22:

GAATGGTACA CGCCCAATGA CGG 23

( 2 ) INFORMATION FOR SEQ ID NO:23:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:23:

CCGTCATTGG GCGTGTACCA TTC 23

( 2 ) INFORMATION FOR SEQ ID NO:24:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( x i ) SEQUENCE DESCRIPTION: SEQ ID NO:24:

GCGGAACATT TATCGGATAT CGGTATTACT GCCGTCTGGA TTC 43

( 2 ) INFORMATION FOR SEQ ID NO:25:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:25:

ATTACCGATA TCCGATAAAT GTTCCGCGTC GTTTTGCAAA CGTTTCCAAT GTTG 54

( 2 ) INFORMATION FOR SEQ ID NO:26:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:26:

GAAAAAACGG GGAAGCCAAT GTTTACGGTA GC 32

( 2 ) INFORMATION FOR SEQ ID NO:27:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:27:

-continued

GCTACCGTAA ACATTGGCTT CCCCGTTTTT TC 32

( 2 ) INFORMATION FOR SEQ ID NO:28:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:28:

CGCTTGAGTC GACTGTCCAA CCATGGTTTA AGCCGCTTGC 40

( 2 ) INFORMATION FOR SEQ ID NO:29:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:29:

GGACGAAAGG AGACCCCCAG CGCGAAATTC 30

( 2 ) INFORMATION FOR SEQ ID NO:30:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:30:

GAATTTCGCG CTGGGGGTCT CCTTTCGTCC CG 32

( 2 ) INFORMATION FOR SEQ ID NO:31:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:31:

CGAAAGGAGA CTCCCCTCGC GAAATTCCTG CCTTG 35

( 2 ) INFORMATION FOR SEQ ID NO:32:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:32:

CAAGGCAGGA ATTTCGCGAG GGGAGTCTCC TTTCG 35

( 2 ) INFORMATION FOR SEQ ID NO:33:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:33:

GGGCGCGGCA ACACATACAG C 21

-continued ( 2 ) INFORMATION FOR SEQ ID NO:34:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:34:

GCTGTATGTG TTGCCGCGCC C 21

( 2 ) INFORMATION FOR SEQ ID NO:35:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:35:

CCGGATTGAT GCTGCGAAAC ACATTAAATT TTCTTTTTTG 40

( 2 ) INFORMATION FOR SEQ ID NO:36:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:36:

TGTGTTTCGC AGCATCAATC CGGAAACCGT CCAATTGC 38

( 2 ) INFORMATION FOR SEQ ID NO:37:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:37:

GACCATCCTG ACGTCGTAGC AGAAATTAAG 30

( 2 ) INFORMATION FOR SEQ ID NO:38:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:38:

TTCTGCTACG ACGTCAGGAT GGTCATAATC 30

AMYLASE VARIANTS

FIELD OF THE INVENTION

Figure 1A:
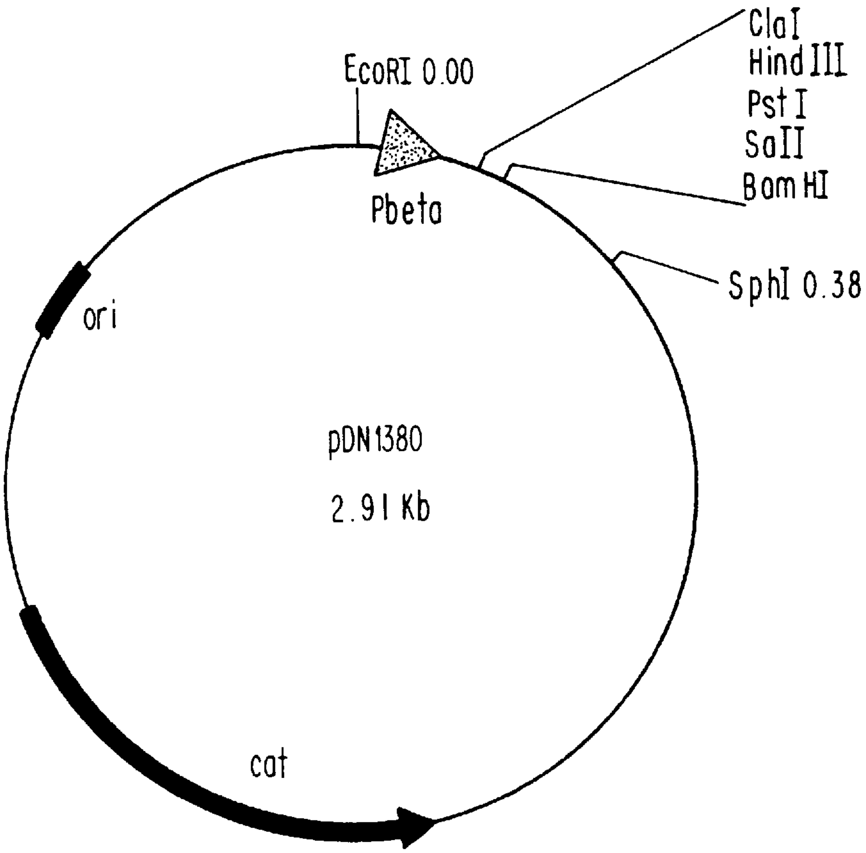

The present invention relates to amylase variants having an improved washing and/or dishwashing performance, to DNA constructs encoding the variants, and to vectors and cells harboring the DNA constructs. Furthermore, the invention relates to methods of producing the amylase variants and to detergent additives and detergent compositions comprising the amylase variants. Finally, the invention relates to the use of the amylase variants for textile desizing.

BACKGROUND OF THE INVENTION

For a number of years α-amylase enzymes have been used for a variety of different purposes, the most important of which are starch liquefaction, textile desizing, starch modification in the paper and pulp industry, and for brewing and baking. A further use of α-amylase, which is becoming increasingly important, is the removal of starchy stains during washing or dishwashing.

In recent years attempts have been made to construct α-amylase variants having improved properties with respect to specific uses such as starch liquefaction and textile desizing.

For instance, U.S. Pat. No. 5,093,257 discloses chimeric α-amylases comprising an N-terminal part of a *B. stearothermophilus* α-amylase and a C-terminal part of a *B. licheniformis* α-amylase. The chimeric α-amylases are stated to have unique properties, such as a different thermostability, as compared to their parent α-amylase. However, all of the specifically described chimeric α-amylases were shown to have a decreased enzymatic activity as compared to their parent α-amylases.

EP 252 666 describes hybrid amylases of the general formula Q-R-L, in which Q is a N-terminal polypeptide residue of from 55 to 60 amino acid residues which is at least 75% homologous to the 57 N-terminal amino acid residues of a specified α-amylase from *B. amyloliquefaciens*, R is a specified polypeptide, and L is a C-terminal polypeptide comprising from 390 to 400 amino acid residues which is at least 75% homologous to the 395 C-terminal amino acid residues of a specified *B. licheniformis* α-amylase.

Suzuki et al. (1989) disclose chimeric α-amylases, in which specified regions of a *B. amyloliqufaciens* α-amylase have been substituted for the corresponding regions of a *B. licheniformis* α-amylase. The chimeric α-amylases were constructed with the purpose of identifying regions responsible for thermostability. Such regions were found to include amino acid residues 177–186 and amino acid residues 255–270 of the *B. amyloliquefaciens* α-amylase. The alterations of amino acid residues in the chimeric α-amylases did not seem to affect properties of the enzymes other than their thermostability.

WO 91/00353 discloses α-amylase mutants which differ from their parent α-amylase in at least one amino acid residue. The α-amylase mutants disclosed in said patent application are stated to exhibit improved properties for application in the degradation of starch and/or textile desizing due to their amino acid substitutions. Some of the mutants exhibit improved stability, but no improvements in enzymatic activity were reported or indicated. The only mutants exemplified are prepared from a parent *B. licheniformis* α-amylase and carry one of the following mutations: H133Y or H133Y+T149I. Another suggested mutation is A111T.

FR 2,676,456 discloses mutants of the *B. licheniformis* α-amylase, in which an amino acid residue in the proximity of His 133 and/or an amino acid residue in the proximity of Ala 209 have been replaced by a more hydrophobic amino acid residue. The resulting α-amylase mutants are stated to have an improved thermostability and to be useful in the textile, paper, brewing and starch liquefaction industry.

EP 285 123 discloses a method of performing random mutagenesis of a nucleotide sequence. As an example of such sequence a nucleotide sequence encoding a *B. stearothermophilus* α-amylase is mentioned. When mutated, an α-amylase variant having improved activity at low pH values is obtained.

In none of the above references is it mentioned or even suggested that α-amylase mutants may be constructed which have improved properties with respect to the detergent industry.

EP 525 610 relates to mutant enzymes having an improved stability towards ionic tensides. The mutant enzymes have been produced by replacing an amino acid residue in the surface part of the parent enzyme with another amino acid residue. The only mutant enzyme specifically described in EP 525 610 is a protease. Amylase is mentioned as an example of an enzyme which may obtain an improved stability towards ionic tensides, but the type of amylase, its origin or specific mutations have not been specified.

WO 94/02597 which was unpublished at the priority dates of the present invention, discloses novel α-amylase mutants which exhibit an improved stability and activity in the presence of oxidizing agents. In the mutant α-amylases, one or more methionine residues have been replaced with amino acid residues different from Cys and Met. The α-amylase mutants are stated to be useful as detergent and/or dishwashing additives as well as for textile desizing.

WO 94/18314 (published only after the priority dates of the present invention) discloses oxidatively stable α-amylase mutants, including mutations in the M197 position of *B. licheniformis* α-amylase.

EP 368 341 describes the use of pullulanase and other amylolytic enzymes optionally in combination with an α-amylase for washing and dishwashing.

The object of the present invention is to provide α-amylase variants which exert an improved washing and/or dishwashing performance compared to their parent α-amylase. Such variant α-amylases have the advantage that they may be employed in a lower dosage than their parent α-amylase. Furthermore, the α-amylase variants may be able to remove starchy stains which cannot or can only with difficulty be removed by α-amylase detergent enzymes known today.

BRIEF DISCLOSURE OF THE INVENTION

The present inventors have surprisingly found that it is possible to improve the washing and/or dishwashing performance of α-amylases by modifying one or more amino acid residues thereof. The present invention is based on this finding.

Accordingly, in a first aspect the present invention relates to a variant of a parent α-amylase enzyme having an improved washing and/or dishwashing performance as compared to the parent enzyme, wherein one or more amino acid residues of the parent enzyme have been replaced by a different amino acid residue and/or wherein one or more amino acid residues of the parent α-amylase have been deleted and/or wherein one or more amino acid residues have been added to the parent α-amylase enzyme, provided that the variant is different from one in which the methionine residue in position 197 of a parent *B. licheniformis* α-amylase has been replaced by alanine or threonine, as the only modification being made.

Except for the disclosure of WO 94/02597, in which replacement of the methionine residue located in position 197 of a *B. licheniformis* α-amylase known as Termamyl® (available from Novo Nordisk A/S, Denmark) by alanine or threonine have been shown to result in an improved performance, as far as the present inventors are aware, no prior disclosure exists which suggests or discloses that washing and/or dishwashing performance of α-amylases may be improved by modifying one or more amino acid residues of the native α-amylase.

In the present context the term "performance" as used in connection with washing and dishwashing is intended to mean an improved removal of starchy stains, i.e. stains containing starch, during washing or dishwashing, respectively. The performance may be determined in conventional washing and dishwashing experiments and the improvement evaluated as a comparison with the performance of the parent unmodified α-amylase. Examples of suitable washing and dishwashing tests are given in the Materials and Methods section and in the examples below. It will be understood that a variety of different characteristics of the α-amylase variant, including specific activity, substrate specificity, Km, Vmax, pI, pH optimum, temperature optimum, thermoactivation, stability towards detergents, etc. taken alone or in combination are involved in providing the improved performance. The skilled person will be aware that the performance of the variant cannot, alone, be predicted on the basis of the above characteristics, but would have to be accompanied by washing and/or dishwashing performance tests.

In the present context the term "variant" is used interchangeably with the term "mutant". The term "variant" is intended to include hybrid α-amylases, i.e. α-amylases comprising parts of at least two different parent α-amylases.

In further aspects the invention relates to a DNA construct comprising a DNA sequence encoding an α-amylase variant of the invention, a recombinant expression vector carrying the DNA construct, a cell which is transformed with the DNA construct or the vector, as well as a method of producing the α-amylase variant by culturing said cell under conditions conducive to the production of the α-amylase variant, after which the α-amylase variant is recovered from the culture.

In a further aspect the invention relates to a method of preparing a variant of a parent α-amylase having improved washing and/or dishwashing performance as compared to the parent α-amylase, which method comprises a) constructing a population of cells containing genes encoding variants of said parent α-amylase, b) screening said population of cells for α-amylase activity under conditions simulating at least one washing and/or dishwashing condition, c) isolating a cell from said population containing a gene encoding a variant of said parent α-amylase which has improved activity as compared with said parent α-amylase under the conditions selected in step b), d) culturing the cell isolated in step c) under suitable conditions in an appropriate culture medium, and e) recovering the α-amylase variant from the culture obtained in step d).

In the present context, the term "simulating at least one washing and/or dishwashing condition" is intended to indicate a simulation of, e.g., the temperature or pH prevailing during washing or dishwashing, as well as the chemical composition of a detergent composition to be used in the washing or dishwashing treatment. The term "chemical composition" is intended to include one, or a combination of two or more, constituents of the detergent composition in question. The constituents of a number of different detergent compositions are listed further below.

The "population of cells" referred to in step a) may suitably be constructed by cloning a DNA sequence encoding a parent α-amylase and subjecting the DNA to site-directed or random mutagenesis as described herein.

In a still further aspect the invention relates to a method of producing a hybrid α-amylase having an improved washing and/or dishwashing performance as compared to any of its parent enzymes, which method comprises a) recombining in vivo or in vitro the N-terminal coding region of an α-amylase gene or corresponding cDNA of one of the parent α-amylases with the C-terminal coding region of an α-amylase gene or corresponding cDNA of another parent α-amylase to form recombinants, b) selecting recombinants that produce a hybrid α-amylase having an improved washing and/or dishwashing performance as compared to any of its parent α-amylases, c) culturing recombinants selected in step b) under suitable conditions in an appropriate culture medium, and d) recovering the hybrid α-amylase from the culture obtained in step c).

In final aspects the invention relates to the use of an α-amylase variant of the invention as a detergent enzyme, in particular for washing or dishwashing, to a detergent additive and a detergent composition comprising the α-amylase variant, and to the use of an α-amylase variant of the invention for textile desizing.

DETAILED DISCLOSURE OF THE INVENTION

Nomenclature

In the present description and claims, the conventional one-letter and three-letter codes for amino acid residues are used. For ease of reference, α-amylase variants of the invention are described by use of the following nomenclature:

Original amino acid(s):position(s):substituted amino acid (s)

According to this nomenclature, for instance the substitution of alanine for asparagine in position 30 is shown as:

Ala 30 Asn or A30N a deletion of alanine in the same position is shown as:

Ala 30 * or A30* and insertion of an additional amino acid residue, such as lysine, is shown as:

Ala 30 AlaLys or A30AK

A deletion of a consecutive stretch of amino acid residues, such as amino acid residues 30–33, is indicated as (30–33)*

Where a specific α-amylase contains a "deletion" in comparison with other α-amylases and an insertion is made in such a position this is indicated as:

* 36 Asp or *36D for insertion of an aspartic acid in position 36

Multiple mutations are separated by plus signs, i.e.:

Ala 30 Asp+Glu 34 Ser or A30N+E34S representing mutations in positions 30 and 34 substituting alanine and glutamic acid for asparagine and serine, respectively.

When one or more alternative amino acid residues may be inserted in a given position it is indicated as A30N,E or A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e. any one of R,N,D,A,C,Q,E, G,H,I,L,K,M,F,P,S,T,W,Y,V The parent α-amylases and variants thereof The α-amylase variant of the invention is preferably prepared on the basis of a parent α-amylase of microbial origin. Thus, the parent α-amylase may be of bacterial origin or may be derived from a fungus including a filamentous fungus or a yeast. The parent α-amylase may be one conventionally used as a detergent enzyme, or one for which such use has never been suggested.

Of particular interest is a parent α-amylase which is derived from a strain of a gram-positive bacterium, such as a strain of Bacillus. Bacillus α-amylases have, in general, been found to have desirable properties with respect to detergent use.

More specifically, the parent bacterial α-amylase may be selected from an α-amylase derived from a strain of *B. licheniformis*, an α-amylase derived from a strain of *B. amyloliquefaciens*, an α-amylase derived from a strain of *B. stearothermophilus* or an α-amylase derived from a strain of *B. subtilis*. In the present context, "derived from" is intended not only to indicate an α-amylase produced or producible by a strain of the organism in question, but also an α-amylase encoded by a DNA sequence isolated from such strain and produced in a host organism transformed with said DNA sequence. Finally, the term is intended to indicate an α-amylase which is encoded by a DNA sequence of synthetic and/or cDNA origin and which has the identifying characteristics of the α-amylase in question.

It has been found that a number of α-amylases produced by Bacillus spp. are highly homologous on the amino acid level. For instance, the *B. licheniformis* α-amylase comprising the amino acid sequence shown in SEQ ID No. 2 has been found to be about 89% homologous with the *B. amyloliquefaciens* α-amylase comprising the amino acid sequence shown in SEQ ID No. 4 and about 79% homologous with the *B. stearothermophilus* α-amylase comprising the amino acid sequence shown in SEQ ID No. 6.

However, other properties of these enzymes are considerably different. Thus, in general the above mentioned *B. licheniformis* α-amylase has been found to have a high pH optimum, a different specificity compared to other Bacillus α-amylases and a low Km which usually is indicative of an excellent substrate binding, whereas the *B. amyloliquefaciens* and the *B. stearothermophilus* α-amylase have a high specific activity and a different starch degradation pattern compared to that of the *B. licheniformis* α-amylase. The *B. stearothermophilus* α-amylase exerts a better washing and/or dishwashing performance than the *B. amyloliquefaciens* α-amylase, but not a performance comparable to the very satisfactory performance of the *B. licheniformis α-amylase.*

In the present invention it has surprisingly been found that the washing and/or dishwashing performance of the satisfactorily performing *B. licheniformis* α-amylase may be further and considerably improved by modifying certain amino acid residues or regions in the amino acid sequence of the α-amylase so as to correspond to a homologous amino acid region in one of the other, more poorly performing Bacillus α-amylases mentioned above.

Thus, in accordance with the present invention it has surprisingly been found possible to use the high degree of amino acid sequence homology observed between the α-amylases produced by the Bacillus spp. *B. licheniformis, B. amyloliquefaciens* and *B. stearothermophilus* to prepare α-amylase variants having improved washing and/or dishwashing performance. More specifically, the variants are prepared on the basis of modification of one or more specific amino acid residues to one or more amino acid residues present in a corresponding or homologous position of the other homologous α-amylases.

For ease of reference, an alignment of the amino acid sequences shown in SEQ ID Nos. 2, 4 and 6, respectively, is shown below. The amino acid numbering of each of the α-amylase sequences is also given. From this alignment homologous positions (and thus homologous amino acid residues) in the sequences may easily be identified.

| SEQUENCE | | Res # |
|---|---|---|
| SEQ ID 6 | AAPFNGTMMQYFEWYLPDDGTLWTKVANEANNLSSLGITA | 40 |
| SEQ ID 4 | ---VNGTLMQYFEWYTPNDGQHWKRLQNDAEHLSDIGITA | 37 |
| SEQ ID 2 | -ANLNGTLMQYFEWYMPNDGQHWRRLQNDSAYLAEHGITA | 39 |
| SEQ ID 6 | LWLPPAYKGTSRSDVGYGVYDLYDLGEFNQKGTVRTKYGT | 80 |
| SEQ ID 4 | VWIPPAYKGLSQSDNGYGPYDLYDLGEFQQKGTVRTKYGT | 77 |
| SEQ ID 2 | VWIPPAYKGTSQADVGYGAYDLYDLGEFHQKGTVRTKYGT | 79 |
| SEQ ID 6 | KAQYLQAIQAAHAAGMQVYADVVFDHKGGADGTEWVDAVE | 120 |
| SEQ ID 4 | KSELQDAIGSLHSRNVQVYGDVVLNHKAGADATEDVTAVE | 117 |
| SEQ ID 2 | KGELQSAIKSLHSRDINVYGDVVINHKGGADATEDVTAVE | 119 |
| SEQ ID 6 | VNPSDRNQEISGTYQIQAWTKFDFPGRGNTYSSFKWRWYH | 160 |
| SEQ ID 4 | VNPANRNQETSEEYQIKAWTDFRFPGRGNTYSDFKWHWYH | 157 |
| SEQ ID 2 | VDPADRNRVISGEHLIKAWTHFHFPGRGSTYSDFKWHWYH | 159 |
| SEQ ID 6 | FDGVDWDESRKLSRIYKFRGIGKAWDWEVDTENGNYDYLM | 200 |
| SEQ ID 4 | FDGADWDESRKISRIFKFRGEGKAWDWEVSSENGNYDYLM | 197 |
| SEQ ID 2 | FDGTDWDESRKLNRIYKFQ--GKAWDWEVSNENGNYDYLM | 197 |
| SEQ ID 6 | YADLDMDHPEVVTELKNWGKWYVNTTNIDGFRLDAVKHIK | 240 |
| SEQ ID 4 | YADVDYDHPDVVAETKKWGIWYANELSLDGFRIDAAKHIK | 237 |
| SEQ ID 2 | YADIDYDHPDVAAEIKRWGTWYANELQLDGFRLDAVKHIK | 237 |
| SEQ ID 6 | FSFFPDWLSYVRSQTGKPLFTVGEYWSYDINKLHNYITKT | 280 |
| SEQ ID 4 | FSFLRDWVQAVRQATGKEMFTVAEYWQNNAGKLENYLNKT | 277 |
| SEQ ID 2 | FSFLRDWVNHVREKTGKEMFTVAEYWQNDLGALENYLNKT | 277 |
| SEQ ID 6 | DGTMSLFDAPLHNKFYTASKSGGAFDMRTLMTNTLMKDQP | 320 |

-continued

| SEQUENCE | | Res # |
|---|---|---|
| SEQ ID 4 | SFNQSVFDVPLHFNLQAASSQGGGYDMRRLLDGTVVSRHP | 317 |
| SEQ ID 2 | NFNHSVFDVPLHYQFHAASTQGGGYDMRKLLNGTVVSKHP | 317 |
| SEQ ID 6 | TLAVTFVDNHDTEPGQALQSWVDPWFKPLAYAFILTRQEG | 360 |
| SEQ ID 4 | EKAVTFVENHDTQPGQSLESTVQTWFKPLAYAFILTRESG | 357 |
| SEQ ID 2 | LKSVTFVDNHDTQPGQSLESTVQTWFKPLAYAFILTRESG | 357 |
| SEQ ID 6 | YPCVFYGDYYGI– – –PQYNIPSLKSKIDPLLIARRDYAYG | 397 |
| SEQ ID 4 | YPQVFYGDMYGTKGTSPKEIPSLKDNIEPILKARKEYAYG | 397 |
| SEQ ID 2 | YPQVFYGDMYGTKGDSQREIPALKHKIEPILKARKQYAYG | 397 |
| SEQ ID 6 | TQHDYLDHSDIIGWTREGGTEKPGSGLAALITDGPGGSKW | 437 |
| SEQ ID 4 | PQHDYIDHPDVIGWTREGDSSAAKSGLAALITDGPGGSKR | 437 |
| SEQ ID 2 | AQHDYFDHHDIVGWTREGDSSVANSGLAALITDGPGGAKR | 437 |
| SEQ ID 6 | MYVGKQHAGKVFYDLTGNRSDTVTINSDGWGEFKVNGGSV | 477 |
| SEQ ID 4 | MYAGLKNAGETWYDITGNRSDTVKIGSDGWGEFHVNDGSV | 477 |
| SEQ ID 2 | MYVGRQNAGETWHDITGNRSEPVVINSEGWGEFHVNGGSV | 477 |
| SEQ ID 6 | SVWVPRKTTVSTIARPITTRPWTGEFVRWTEPRLVAWP | 515 |
| SEQ ID 4 | SIYVQK | 483 |
| SEQ ID 2 | SIYVQR | 483 |

Although the present invention is illustrated on the basis of modifications of the *B. licheniformis* α-amylase having the amino acid sequence shown in SEQ ID No. 2 (commercially available from Novo Nordisk A/S, Denmark as Termamyl®), it will be understood that analogues of said α-amylase may be modified correspondingly to create variants with improved washing and/or dishwashing performance. Thus, whenever reference is made to a specific modification of the *B. licheniformis* α-amylase it will be understood that an analogous α-amylase may be modified analogously.

In the present context, the term "analogue" is intended to indicate an α-amylase which i) is at least 60% homologous with the sequence shown in SEQ ID No. 2, and/or ii) exhibits immunological cross-reactivity with an antibody raised against the said α-amylase, and/or iii) is encoded by a DNA sequence which hybridizes with the same probe as the DNA sequence encoding the said α-amylase, which latter DNA sequence is shown in SEQ ID No. 1.

Property i) of said analogue of the *B. licheniformis* α-amylase having the sequence shown in SEQ ID No. 2 is intended to indicate the degree of identity between the analogue and the *B. licheniformis* α-amylase indicating a derivation of the first sequence from the second. In particular, a polypeptide is considered to be homologous with the *B. licheniformis* α-amylase if a comparison of the respective amino acid sequences reveals a degree of sequence identity of greater than about 60%, such as above 70%, 80%, 85%, 90% or even 95%. Sequence comparisons can be performed via known algorithms, such as the one described by Lipman and Pearson (1985).

Said analogues of the *B. licheniformis* α-amylase comprising the amino acid sequence shown in SEQ ID No. 2 as defined by property i) above are therefore intended to comprise a homologous α-amylase derived from other Bacillus spp. than *B. licheniformis*, e.g. from *B. amyloliquefaciens* or *B. stearothermophilus*. Furthermore, the analogue may be a *B. licheniformis* α-amylase having an amino acid sequence different from, but homologous with, that shown in SEQ ID No. 2. An example of such an α-amylase is that produced by the *B. licheniformis* described in EP 252 666 (ATCC 27811), and those identified in WO 91/00353 and WO 94/18314. Other specific examples of analogues of the *B. licheniformis* α-amylase comprising the amino acid sequence shown in SEQ ID No. 2 are Optitherm® and Takatherm® (available from Solvay), Maxamyl® (available from Gist-Brocades), Spezym AA® (available from Genencor), and Keistase® (available from Daiwa).

Finally, the α-amylase analogue may be a genetically engineered α-amylase, e.g. any of those mentioned in the above described prior art references or a variant of any of the above specified *B. licheniformis* α-amylases. Typically, a genetically engineered α-amylase will have been prepared in order to improve one or more properties such as thermostability, acid/alkaline stability, temperature, pH optimum, and the like.

The properties ii) and iii) of said analogue of the *B. licheniformis* α-amylase comprising the amino acid sequence shown in SEQ ID No. 2 may be determined as follows:

Property ii) of said analogue, i.e. the immunological cross reactivity, may be assayed using an antibody raised against or reactive with at least one epitope of the *B. licheniformis* α-amylase comprising the amino acid sequence shown in SEQ ID No. 2. The antibody, which may either be monoclonal or polyclonal, may be produced by methods known in the art, e.g. as described by Hudson et al., 1989. The immunological cross-reactivity may be determined using assays known in the art, examples of which are Western Blotting or radial immunodiffusion assay, e.g. as described by Hudson et al., 1989. In this respect, immunological cross-reactivity between the α-amylases having the amino acid sequences SEQ ID Nos. 2, 4 and 6, respectively, has been found.

The oligonucleotide probe used in the characterization of the analogue in accordance with property iii) defined above may suitably be prepared on the basis of the full or partial nucleotide or amino acid sequence shown in SEQ ID No. 1 and 2, encoding or constituting, respectively, the *B. licheniformis* α-amylase. Suitable conditions for testing hybridization involve presoaking in 5×SSC and prehybridizing for 1 h at ~40° C. in a solution of 20% formamide, 5×Denhardt's solution, 50 mM sodium phosphate, pH 6.8, and 50 μg of denatured sonicated calf thymus DNA, followed by hybridization in the same solution supplemented with 100 μM ATP for 18 h at ~40° C., or other methods described by e.g. Sambrook et al., 1989.

The present inventors have surprisingly found that modification of one or more amino acid residues in the N-terminal part of the *B. licheniformis* α-amylase comprising the amino acid sequence shown in SEQ ID No. 2 results in improved washing and/or dishwashing performance of the resulting variant α-amylase.

This finding is surprising in that the N-terminal part of the α-amylase in a spatial model has been found to be located at a position remote from the active site of the molecule, indicating little importance of this region for activity. The spatial model of *B. licheniformis* α-amylase was built using, as scaffold, the *Aspergillus oryzae* α-amylase X-ray structure, 2TAA.PDB, from the protein databank, Brookhaven National Laboratories. Only regions around the B-barrel "domain" were built. The model was made by incorporating two minor deletions in the N-terminal part and a large insertion (30 residues) in the middle part of the *B. licheniformis* α-amylase sequence compared to that of the *A. oryzae* α-amylase.

In accordance with the above finding, and in a specific embodiment, the invention relates to a variant of a parent α-amylase comprising the amino acid sequence shown in SEQ ID No. 2, or a variant of an analogue of said parent α-amylase, which variant has improved washing and/or dishwashing performance and which comprises at least one substitution, deletion or addition in the N-terminal end of the parent α-amylase, in particular within the first 50 N-terminal amino acid residues of amino acid sequence of the mature α-amylase.

More particularly, a variant of the parent *B. licheniformis* α-amylase comprising the amino acid sequence shown in SEQ ID No. 2, or a variant of an analogue of said parent α-amylase, in which at least one amino acid residue located in position 17–35, such as position 20–35, of said parent α-amylase has been substituted or deleted, or in which at least one amino acid has been added to said parent α-amylase within the amino acid segment located in position 17–35 (such as 20–35), has been found to be of interest.

This segment constitutes a region of a relatively low degree of homology in the otherwise highly conserved N-terminal part of the α-amylases derived from *B. licheniformis, B. amyloliquefaciens* and *B. stearothermophilus*. It has been found that amino acid substitutions within this region of the *B. licheniformis* α-amylase, in particular to amino acid residues located in the homologous position in *B. amyloliquefaciens* and *B. stearothermophilus* α-amylase, lead to α-amylase variants with improved properties.

In particular, the region defined by amino acid residues 29≧35 of the *B. licheniformis* α-amylase comprising the amino acid sequence shown in SEQ ID No. 2 comprises a large number of positions in which no homology exists between the various Bacillus α-amylases. Accordingly, the *B. licheniformis* α-amylase variant of the invention may be a variant in which at least one amino acid residue located in position 29≧35 of the parent α-amylase has been substituted or deleted, or in which at least one amino acid has been added to the parent α-amylase within the amino acid segment located in position 29–35.

More specifically, the *B. licheniformis* α-amylase variant of the invention may be one in which the amino acid residue(s) located in one or more of the following positions have been modified, i.e. deleted or replaced by any other amino acid residue as explained above:

N17, R23, S29, A30, Y31, A33, E34, H35

As a preferred example of a *B. licheniformis* α-amylase variant of the invention may be mentioned a variant which comprises at least one of the following mutations:

R23K,T

S29A

A30E,N

Y31H,NA33SE34D,S

H35I,L; or any combination of these mutations.

In example 1 below, the construction of a number of different *B. licheniformis* α-amylase variants is described, which variants have been modified by one or more amino acid substitutions or deletions within the N-terminal end region of the *B. licheniformis* α-amylase. All of these variants have been found to have an improved washing and/or dishwashing performance as compared to their parent α-amylase.

Furthermore, other specific amino acid residues or regions of interest of the *B. licheniformis* α-amylase comprising the amino acid sequence shown in SEQ ID No. 2 or an analogue thereof are listed below, together with preferred modifications of these amino acid residues or regions. Accordingly, in a further embodiment the present invention relates to a *B. licheniformis* α-amylase variant which comprises at least one modification of an amino acid residue or region listed below. The variant comprises at least one, or a combination of two or more, of the specific amino acid modifications mentioned below:

a) modification of an amino acid residue located in position 1, 2, 3 and/or 15; accordingly, a *B. licheniformis* α-amylase variant of interest is one which comprises a mutation in position A1, N2, L3 or M15 of the parent α-amylase, preferably one or more of the mutations A1V, M15T,L, N2*, L3V or A1*+N2*;

b) modification of amino acid residues located in the region spanning amino acid residues 51–58, in particular an amino acid residue located in position 51, 52 and/or 58 thereof, e.g. at least one of the following mutations: Q51R, A52S, A58P,V;

c) modification of the amino acid residue H68, in particular one of the following mutations: H68N,Q;

d) modification of amino acid residues located in position 85 and/or 88, in particular at least one of the mutations S85Q, K88Q;

e) modification of amino acid residues located in the region 94–104, in particular an amino acid residue located in position 94, 95, 96, 99, 103 and/or 104 thereof, e.g. at least one of the following mutations: N96Q, G99A, I103F, N104D;

f) modification of amino acid residues located in the region 121–136, in particular an amino acid residue located in position 121, 127, 128, 131, 132, 133 and/or 134 thereof, e.g. at least one of the mutations D121N, R127Q, V128E, G131E, E132T, H133Y, L134Q, K136Q;

g) modification of amino acid residues located in position 140, 142, 148 and/or 152, e.g. at least one of the following mutations: H140K, H142D, D152S, S148N;

h) modification of amino acid residues located in the region 142–182, in particular a deletion of all or a substantial part of the amino acid residues in the said region;

i) modification of amino acid residues located in the region 172–178, in particular an amino acid residue located in the position 172, 175, 177 and/or 178, e.g. at least one of the following mutations: N172S, P177FRG, Q178I,E;

j) modification of amino acid residues S187, A209 and/or T217, in particular the mutation S187D, A209V and/or T217K;

k) modification of amino acid residue R242, in particular the mutation R242P;

l) modification of an amino acid residue located in the region 246–251, in particular an amino acid residue located in the position 246, 247, 250 and/or 251, e.g. H247A,Y, E250Q,S, K251A,Q m) modification of amino acid residue E255, in particular the mutation E255P;

n) modification of an amino acid residue located in the region 260–269, in particular an amino acid residue located in position 260, 264, 265, 267, 268, and/or 269, e.g. at least one of the following mutations: A260G, N265Y, A269K;

o) modification of an amino acid residue located in the region 290–293, in particular an amino acid residue located in position 290, 291 and/or 293, e.g. at least one of the following mutations: Y290F,N, Q291K, H293Q, Y;

p) modification of an amino acid residue located in the region 314–320, in particular an amino acid residue in position 315, 318 and/or 320, e.g. the following mutations: K315D, L318T and/or S320A;

q) modification of amino acid residues T341 and/or Q360, in particular the mutation T341P and/or Q360C;

r) modification of an amino acid residue located in the region 369–383, in particular an amino acid residue in position 370, 371, 372, 373, 374, 375, 376, 379 and/or 382, e.g. at least one of the following mutations: 370*, 371*, 372*, (370–372)*, S373P, Q374P, R375Y, A379S, H382S;

s) modification of an amino acid residue located in position 393, 398 and/or 409, e.g. the mutations Q393D, A398T,P and/or V409I;

t) modification of an amino acid residue located in the region 416–421, in particular an amino acid residue located in position 419, 420 and/or 421, e.g. at least one of the following mutations: V419K, A420P, N421G;

u) modification of amino acid residues A435 and/or H450, in particular the mutations A435S and/or H450Y;

v) modification of an amino acid residue located in the region 458–465, in particular an amino acid residue located in position 458, 459 and/or 461, e.g. at least one of the following mutations: P459T, V461K,T;

w) modification of the amino acid residue M197 in combination with at least one further mutation, including a deletion or replacement, of an additional amino acid residue of the amino acid sequence and/or an addition of at least one amino acid residue within the sequence, or at the C-terminal and/or N-terminal end of the amino acid sequence.

Specific examples of α-amylase variants as defined in w) above include variants comprising one of the mutations M197T,G,I,L,A,S,N,C in combination with any other mutation defined herein.

Based on the spatial model of the *B. licheniformis* α-amylase referred to above, it is presently contemplated that the deletion mentioned in h) above may result in an improved accessability to the active site, thereby improving the substrate specificity without, however, changing the thermoactivation to any substantial extent.

Normally, it is found that insertion of additional proline residues in enzymes results in a stabilization of the enzyme at elevated temperatures, possibly due to the fact that a high number of proline residues makes the structure of the enzyme more rigid at elevated temperatures. In the present invention it has surprisingly been found that insertion of additional proline residues in the *B. licheniformis* α-amylase results in a destabilization of the resulting variant at elevated temperatures. Thus, by insertion of proline residues the temperature optimum of the resulting variant is lowered.

It has surprisingly been found that proline-substituted variants of the *B. licheniformis* α-amylase with a lowered temperature optimum show considerably improved washing and/or dishwashing performance.

When the parent α-amylase is a *B. licheniformis* α-amylase, the non-proline amino acid residue to be replaced with proline is preferably located in a position which in other α-amylases, such as a *B. amyloliquefaciens* or *B. stearothermophilus* α-amylase, is occupied by proline.

Accordingly, in an important embodiment the variant of the invention is one in which one or more non-proline residues have been substituted for proline residues. When the parent α-amylase is the *B. licheniformis* α-amylase, mutations of interest include: R242P, E255P, T341P, S373P, Q374P, A420P, Q482P.

Finally, on the basis of the spatial model of the *B. licheniformis* α-amylase referred to above, it is contemplated that the variants prepared by the following amino acid substitutions in the substrate binding area have an improved (higher) pH optimum with respect to dishwashing/washing performance:

R23E,D, K106E,D, I135E,D, K156E,D, V186E,D, Y198E,D, Y193E,D, Q178E,D, K234E,D, K237E,D and/or Q360E,D.

As mentioned above, one example of an analogous amylase is a *B. amyloliquefaciens* α-amylase. Another is a *B. stearothermophilus* αamylase. The amino acid sequences of a *B. amyloliquefaciens* α-amylase and a *B. stearothermophilus* α-amylase are shown in SEQ ID No. 4 and SEQ ID No. 6, respectively. The terms *B. amyloliquefaciens* α-amylase and *B. stearothermophilus* α-amylase, respectively, are intended to include analogues of these α-amylases which i) have an amino acid sequence which is at least 60% homologous, such as at least 70%, 75%, 80%, 85%, 90% or 95% homologous, with the sequences shown in SEQ ID No. 4 and 6, respectively, and/or ii) exhibit immunological cross-reactivity with an antibody raised against said α-amylase, and/or iii) are encoded by a DNA sequence which hybridizes with the same probe as the DNA sequence encoding said α-amylase, which latter DNA sequence is shown in SEQ ID No. 3 and 5, respectively.

Properties i)–iii) are to be understood in the same manner as explained above in connection with the *B. licheniformis* α-amylase. Specific examples of analogues of the *B. amyloliquefaciens* α-amylase comprising the amino acid sequence shown in SEQ ID No. 4 are BAN® (available from Novo Nordisk A/S), Optiamyl® (available from Solvay), Dexlo® and Rapidase® (available from Gist-Brocades) and Kazuzase® (a mixed α-amylase and protease product available from Showa Denko). Specific examples of analogues of the *B. stearothermophilus* α-amylase comprising the amino acid sequence shown in SEQ ID No. 6 are Liquozyme 280L® (available from Novo Nordisk A/S) and G-zyme 995® (available from Enzyme BioSystems).

It is contemplated that the principles disclosed herein for preparation of variants with improved washing and/or dishwashing performance may be used for preparing variants of the closely related *B. amyloliquefaciens* and the *B. stearothermophilus* α-amylases. Thus, for instance, amino acid residues located in positions in the *B. amyloliquefaciens* or *B. stearothermophilus* α-amylase homologous to the *B. licheniformis* amino acid residues mentioned above may be substituted with similar amino acid residues, thereby giving rise to novel variants with improved properties.

Homologous positions may be identified by a comparison of the primary structures (cf. the comparison between SEQ ID Nos. 2, 4 and 6 given hereinbefore) or of the tertiary structures of the α-amylases in question.

Homologous positions in the tertiary structure may be determined by comparison with the established crystal structure of other α-amylases, such as the *A. oryzae* α-amylase structure (referred to above) or the *A. niger* α-amylase structure (Boel et al., 1990, Biochemistry 29, pp. 6244–6249.

Furthermore, it is contemplated that the above described principles for preparing α-amylase variants having improved washing and/or dishwashing performance may be used for preparing variants of other α-amylases such as an α-amylase derived from *B. subtilis* or from a strain of Aspergillus such as a strain of *A. niger*, e.g. the α-amylase described in Danish Patent Application DK 5126/87, or *A. oryzae*, e.g. the commercially available Fungamyl® (Novo Nordisk A/S) having the amino acid sequence shown in SEQ ID No. 7, Mycolase® (Gist-Brocades), Clarase (Solvay), and Phlowzyme® (Enzyme BioSystems).

As mentioned above, the α-amylase variant of the invention may be a hybrid α-amylase. Accordingly, in a further embodiment the variant of the invention having an improved washing and/or dishwashing performance is a hybrid α-amylase comprising a combination of partial amino acid sequences derived from at least two parent α-amylases. In the context of hybrid amylases, the term "improved washing and/or dishwashing performance" is intended to indicate that the performance of the hybrid is better than that of any of the parent amylases when tested under similar conditions.

As far as the present inventors are aware, no prior disclosure or suggestion of hybrid α-amylases having improved washing and/or dishwashing performance exists. In fact, hybrid α-amylases have never previously been described or suggested for use in washing or dishwashing.

Preferably, at least one of the parent α-amylases of the hybrid is a microbial α-amylase (the other parent, e.g., being of mammalian origin); more preferably, all of the parent α-amylases are of microbial origin. In one embodiment it is preferred that the hybrid α-amylase comprises a combination of partial amino acid sequences derived from at least two bacterial α-amylases, from at least one bacterial and one fungal α-amylase, or from at least two fungal α-amylases.

A preferred example of a hybrid α-amylase of the invention is one which comprises a C-terminal part of an α-amylase derived from a strain of *B. licheniformis*, and a N-terminal part of an α-amylase derived from a strain of *B. amyloliquefaciens* or from a strain of *B. stearothermophilus*.

Preferably, the *B. licheniformis* α-amylase and/or the *B. amyloliquefaciens* and/or *B. stearothermophilus* α-amylases are those comprising the amino acid sequences shown in SEQ ID Nos. 2, 4 and 6, respectively, or an analogue of any of said α-amylases as defined in further detail hereinbefore. It will be understood that the hybrid α-amylase of the invention may comprise partial sequences of two parent α-amylases, as well as of three or more parent α-amylases. Furthermore, the hybrid α-amylase of the invention may comprise one, two or more parts of each of the parent aα-amylases, such as, e.g., an N-terminal part of a first parent α-amylase, intermediate parts of a second parent α-amylase and optionally further intermediate parts of the first, third or further parent α-amylases, and finally a C-terminal part of any of these parent α-amylases.

A particularly preferred hybrid α-amylase of the invention is one which comprises at least 410, e.g. 415, such as at least 430, at least 445, e.g. 446, or at least 460 amino acid residues of the C-terminal part of the *B. licheniformis* α-amylase comprising the amino acid sequence shown in SEQ ID No. 2 or an analogue thereof as defined herein. The N-terminal part of the hybrid α-amylase is preferably derived from the *B. amyloliquefaciens* or *B. stearothermophilus* α-amylase.

In a further embodiment the invention relates to a hybrid α-amylase as defined above which in addition comprises one or more mutations, e.g. prepared by site-specific or random mutagenesis. Of particular interest is a hybrid α-amylase as described above comprising a C-terminal part of the α-amylase having the amino acid sequence shown in SEQ ID No. 2, in which the methionine residue in position 197 has been replaced with another amino acid residue. Specific examples of desirable mutations are M197T, M197G, M197L, M197A, M197N and M197S.

It should be noted that, according to the invention, any one of the modifications of the amino acid sequence indicated above for the α-amylase variants (and hybrid α-amylases) may be combined with any one of the other modifications mentioned above, where appropriate.

The present inventors have found that an apparent relationship exists between the washing and/or dishwashing performance of a given enzyme and the hydrolysis velocity obtained in a given reaction.

More specifically, it has been found that the higher the hydrolysis velocity, the better the washing and/or dishwashing performance which is obtained. Thus, without being limited to any theory it is contemplated that the improvement of washing and/or dishwashing performance obtained with an α-amylase variant of the invention as compared to that of the parent α-amylase may be directly predicted by comparing the hydrolysis velocity obtained for the variant and the parent α-amylase, respectively, when tested under similar conditions. The hydrolysis velocity may be calculated by use of the Michaelis-Menten equation, c.f. Example 11 below.

From the equation given in Example 11 it will be apparent that at low substrate concentrations, the hydrolysis velocity is directly proportional to Vmax and is inversely proportional to Km.

Accordingly, the α-amylase variant of the invention is preferably one which at low substrate concentrations has a higher hydrolysis velocity than the parent α-amylase. Alternatively, the α-amylase variant of the invention is preferably one which has a higher Vmax and/or a lower Km than the parent α-amylase when tested under the same conditions. In the case of a hybrid α-amylase, the parent α-amylase to be used for the comparison should be the one of the parent enzymes having the best performance.

The Vmax, Km and V may be determined by well-known procedures, e.g. by the method described in Example 11 below.

Methods of preparing α-amylase variants

Several methods for introducing mutations into genes are known in the art. After a brief discussion of the cloning of α-amylase-encoding DNA sequences (which for instance encode functional analogues of the Bacillus α-amylases disclosed herein), methods for generating mutations at specific sites within the α-amylase-encoding sequence will be discussed.

Cloning a DNA sequence encoding an α-amylase

The DNA sequence encoding a parent α-amylase may be isolated from any cell or microorganism producing the α-amylase in question, using various methods well known in the art. First, a genomic DNA and/or cDNA library should be constructed using chromosomal DNA or messenger RNA from the organism that produces the α-amylase to be studied. Then, if the amino acid sequence of the α-amylase is known, homologous, labelled oligonucleotide probes may be synthesized and used to identify α-amylase-encoding clones from a genomic library prepared from the organism in question. Alternatively, a labelled oligonucleotide probe containing sequences homologous to a known α-amylase gene could be used as a probe to identify α-amylase-encoding clones, using hybridization and washing conditions of lower stringency.

Yet another method for identifying α-amylase-encoding clones would involve inserting fragments of genomic DNA into an expression vector, such as a plasmid, transforming α-amylase-negative bacteria with the resulting genomic DNA library, and then plating the transformed bacteria onto agar containing a substrate for α-amylase, thereby allowing clones expressing the α-amylase to be identified.

Alternatively, the DNA sequence encoding the enzyme may be prepared synthetically by established standard methods, e.g. the phosphoaridite method described by S. L. Beaucage and M. H. Caruthers (1981) or the method described by Matthes et al. (1984). In the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

Site-directed mutagenesis

Once an α-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the α-amylase-encoding sequence, is created in a vector carrying the α-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into α-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random mutagenesis

Random mutations may be introduced in a DNA sequence encoding a parent α-amylase by subjecting the DNA sequence to a suitable physical or chemical mutagenic agent such as UV irradiation, ethyl methanesulfonate (EMS), sodium bisulphite or any other mutagenic agent known in the art, or by subjecting the DNA sequence to directed random mutagenesis by use of PCR using degenerate oligonucleotides for the introduction of mutations in a specified region.

Methods of preparing hybrid α-amylases

As an alternative to site-specific mutagenesis, α-amylase variants which are hybrids of at least two of parent α-amylases may be prepared by combining the relevant parts of the respective genes in question.

Naturally occurring enzymes may be genetically modified by random or site directed mutagenesis as described above. Alternatively, part of one enzyme may be replaced by a part of another to obtain a chimeric enzyme. This replacement can be achieved either by conventional in vitro gene splicing techniques or by in vivo recombination or by combinations of both techniques. When using conventional in vitro gene splicing techniques, a desired portion of the α-amylase gene coding sequence may be deleted using appropriate site-specific restriction enzymes; the deleted portion of the coding sequence may then be replaced by the insertion of a desired portion of a different α-amylase coding sequence so that a chimeric nucleotide sequence encoding a new α-amylase is produced. Alternatively, α-amylase genes may be fused, e.g. by use of the PCR overlay extension method described by Higuchi et al. 1988.

The in vivo recombination techniques depend on the fact that different DNA segments with highly homologous regions (identity of DNA sequence) may recombine, i.e. break and exchange DNA, and establish new bonds in the homologous regions. Accordingly, when the coding sequences for two different but homologous amylase enzymes are used to transform a host cell, recombination of homologous sequences in vivo will result in the production of chimeric gene sequences. Translation of these coding sequences by the host cell will result in production of a chimeric amylase gene product. Specific in vivo recombination techniques are described in U.S. Pat. No. 5,093,257 and EP 252 666.

The α-amylase genes from *B. licheniformis* and from *B. amyloliquefaciens* are approximately 70 percent homologous at the DNA level and suitable for hybrid formation by in vivo gene splicing.

In an alternative embodiment, the hybrid enzyme may be synthesized by standard chemical methods known in the art. For example, see Hunkapiller et al. (1984). Accordingly, peptides having the amino acid sequences described above may be synthesized in whole or in part and joined to form the hybrid enzymes of the invention.

Screening for or selection of variants of the invention

The screening for or selection of variants (including hybrids) of the invention may suitably be performed by determining the starch-degrading activity of the variant, for instance by growing host cells transformed with a DNA sequence encoding a variant on a starch-containing agarose plate and identifying starch-degrading host cells. Furthermore, the selection or screening may suitably involve testing of one or more parameters of importance in connection with washing and/or dishwashing performance. Such parameters may, e.g., include the specific activity, the substrate specificity, the thermoactivation, the pH optimum, the temperature optimum, the tolerance towards constituents of conventionally used detergent compositions (e.g. of the types mentioned further below) and any other parameter considered to be of importance for washing and/or dishwashing performance. All of these parameters may be determined in accordance with well-known principles. Finally, the performance of the variant may be tested by use of a suitable washing and/or dishwashing assay, e.g. as described in the Materials and Methods section below.

Expression of α-amylase variants

According to the invention, a mutated α-amylase-encoding DNA sequence produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an α-amylase variant of the invention encoding may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding an α-amylase variant of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus Amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the α-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such. as ampicillin, kanamycin, chloramphenicol or tetracycline resistance. Furthermore, the vector may comprise Aspergillus selection markers such as amdS, argB, niad and sC, a marker giving rise to hygromycin resistance, or the selection may be accomplished by co-transformation, e.g. as described in WO 91/17243.

While intracellular expression may be advantageous in some respects, e.g. when using certain bacteria as host cells, it is generally preferred that the expression is extracellular. In general, the Bacillus α-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding an α-amylase variant, the promoter, terminator and other elements, respectively, and to insert them into suitable vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of an α-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram negative bacteria such as *E. coli*. The transformation of the bacteria may, for instance, be effected by protoplast transformation or by using competent cells in a manner known per se.

The yeast organism may favorably be selected from a species of Saccharomyces or Schizosaccharomyces, e.g. *Saccharomyces cerevisiae*. The filamentous fungus may advantageously belong to a species of Aspergillus, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing an α-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the α-amylase variant of the invention. Suitable media are available from commercial suppliers or may be prepared according to published recipes (e.g. as described in catalogues of the American Type Culture Collection).

The α-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Detergent Additive and Composition for Dishwashing and Washing

Due to their improved washing and/or dishwashing performance, α-amylase variants (including hybrids) of the invention are particularly well suited for incorporation into detergent compositions, e.g. detergent compositions intended for performance in the range of pH 7–13, particularly the range of pH 8–11.

According to the invention, the α-amylase variant may be added as a component of a detergent composition. As such, it may be included in the detergent composition in the form of a detergent additive. The detergent composition as well as the detergent additive may additionally comprise one or more other enzymes conventionally used in detergents, such as proteases, lipases, amylolytic enzymes, oxidases (including peroxidases), or cellulases.

It has been found that substantial improvements in washing and/or dishwashing performance may be obtained when α-amylase is combined with another amylolytic enzyme, such as a pullulanase, an iso-amylase, a betα-amylase, an amyloglucosidase or a CTGase. Examples of commercially available amylolytic enzymes suitable for the given purpose are AMG®, Novamyl® and Promozyme®, all available from Novo Nordisk A/S.

Accordingly, in a particular embodiment the invention relates to a detergent additive comprising an α-amylase variant of the invention in combination with at least one other amylolytic enzyme (e.g. chosen amongst those mentioned above).

In a specific aspect, the invention provides a detergent additive. The enzymes may be included in a detergent composition by adding separate additives containing one or more enzymes, or by adding a combined additive comprising all of these enzymes. A detergent additive of the invention, i.e. a separated additive or a combined additive, can be formulated, e.g., as a granulate, liquid, slurry, etc. Preferred detergent additive formulations are granulates (in particular non-dusting granulates), liquids (in particular stabilized liquids), slurries or protected enzymes.

Non-dusting granulates may be produced, e.g., as disclosed in U.S. Pat. No. 4,106,991 and U.S. Pat. No. 4,661,452, and may optionally be coated by methods known in the art. The detergent enzymes may be mixed before or after granulation.

Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238 216.

In a still further aspect, the invention relates to a detergent composition comprising an α-amylase variant (including hybrid) of the invention.

The detergent composition of the invention may be in any convenient form, e.g. as powder, granules or liquid. A liquid detergent may be aqueous, typically containing up to 90% of water and 0–20% of organic solvent, or non-aqueous, e.g. as described in EP Patent 120,659.

Washing detergent composition

The washing detergent composition (i.e. a composition useful for laundry washing) comprises a surfactant which may be anionic, non-ionic, cationic, amphoteric or a mixture of these types. The detergent will usually contain 0–50% of anionic surfactant such as linear alkylbenzene sulfonate, α-olefinsulfonate, alkyl sulfate, alcohol ethoxy sulfate or soap. It may also contain 0–40% of non-ionic surfactant such as nonyl phenol ethoxylate or alcohol ethoxylate. Furthermore, it may contain an N-(polyhydroxyalkyl)-fatty acid amide surfactant (e.g. as described in WO 92/06154).

The detergent may contain 1–40% of detergent builders such as zeolite, di- or triphosphate, phosphonate, citrate, NTA, EDTA or DTPA, alkenyl succinic anhydride, or silicate, or it may be unbuilt (i.e. essentially free of a detergent builder).

The detergent composition of the invention may be stabilized using conventional stabilizing agents for the enzyme (s), e.g. a polyol such as e.g. propylene glycol, a sugar or sugar alcohol, lactic acid, boric acid, or a boric acid derivative, e.g. an aromatic borate ester, and the composition may be formulated as described in e.g. WO 92/19709 or WO 92/19708. Other enzyme stabilizers are well known in the art.

The detergent composition of the invention may contain bleaching agents, e.g. perborate, percarbonate and/or activator, tetraacetyl ethylene diamine, or nonanoyloxybenzene sulfonate, and may be formulated as described in, e.g., WO 92/07057.

The detergent composition of the invention may also contain other conventional detergent ingredients, e.g. deflocculating polymers, fabric conditioners, foam boosters, foam depressors, anti-corrosion agents, soil-suspending agents, sequestering agents, anti-soil redeposition agents, dyes, bactericides, optical brighteners and perfumes, as well as enzymes as mentioned above.

Particular forms of detergent composition within the scope of the invention and containing an α-amylase variant of the invention include:

a) A detergent composition formulated as a detergent powder containing phosphate builder, anionic surfactant, nonionic surfactant, silicate, alkali to adjust to desired pH in use, and neutral inorganic salt.

b) A detergent composition formulated as a detergent powder containing zeolite builder, anionic surfactant, nonionic surfactant, acrylic or equivalent polymer, silicate, alkali to adjust to desired pH in use, and neutral inorganic salt.

c) A detergent composition formulated as an aqueous detergent liquid comprising anionic surfactant, nonionic surfactant, organic acid, alkali, with a pH in use adjusted to a value between 7 and 11.

d) A detergent composition formulated as a nonaqueous detergent liquid comprising a liquid nonionic surfactant consisting essentially of linear alkoxylated primary alcohol, phosphate builder, alkali, with a pH in use adjusted to a value between about 7 and 11.

e) A compact detergent composition formulated as a detergent powder in the form of a granulate having a bulk density of at least 600 g/l, containing anionic surfactant and nonionic surfactant, phosphate builder, sodium silicate, and little or substantially no neutral inorganic salt.

f) A compact detergent composition formulated as a detergent powder in the form of a granulate having a bulk density of at least 600 g/l, containing anionic surfactant and nonionic surfactant, zeolite builder, sodium silicate, and little or substantially no neutral inorganic salt.

g) A detergent composition formulated as a detergent powder containing anionic surfactant, nonionic surfactant, acrylic polymer, fatty acid soap, sodium carbonate, sodium sulfate, clay particles, and sodium silicate.

h) A liquid compact detergent comprising 5–65% by weight of surfactant, 0–50% by weight of builder and 0–30% by weight of electrolyte.

i) A compact granular detergent comprising linear alkyl benzene sulphonate, tallow alkyl sulphate, $C_{4-5}$ alkyl sulphate, $C_{4-5}$ alcohol 7 times ethoxylated, tallow alcohol 11 times ethoxylated, dispersant, silicone fluid, trisodium citrate, citric acid, zeolite, maleic acid acrylic acid copolymer, DETMPA, cellulase, protease, lipase, an amylolytic enzyme, sodium silicate, sodium sulphate, PVP, perborate and accelerator.

j) A granular detergent comprising sodium linear $C_{1-2}$ alkyl benzene sulfonate, sodium sulfate, zeolite A, sodium nitrilotriacetate, cellulase, PVP, TAED, boric acid, perborate and accelerator.

k) A liquid detergent comprising $C_{12-14}$ alkenyl succinic acid, citric acid monohydrate, sodium $C_{12-15}$ alkyl sulphate, sodium sulfate of $C_{12-15}$ alcohol 2 times ethoxylated, $C_{12-15}$ alcohol 7 times ethoxylated, $C_{12-15}$ alcohol 5 times ethoxylated, diethylene triamine penta (methylene phosphonic acid), oleic acid, ethanol, propanediol, protease, cellulase, PVP, suds supressor, NaOH, perborate and accelerator.

Furthermore, examples of suitable detergent compositions in which α-amylase variants of the invention may advantageously be included comprise the detergent compositions described in EP 373 850, EP 378 261, WO 92/19709, EP 381 397, EP 486 073, WO 92/19707, EP 407 225, and WO 92/13054.

Dishwashing Composition

The dishwashing detergent composition comprises a surfactant which may be anionic, non-ionic, cationic, amphoteric or a mixture of these types. The detergent will contain 0–90% of non-ionic surfactant such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains 1–90% of detergent builders.

Examples of phosphorus-containing inorganic alkaline detergent builders, when present, include the water-soluble salts especially alkali metal pyrophosphates, orthophosphates, polyphosphates, and phosphonates. Examples of non-phosphorus-containing inorganic builders, when present, include water-soluble alkali metal carbonates, borates and silicates as well as the various types of water-insoluble crystalline or amorphous alumino silicates of which zeolites are the best-known representatives.

Examples of suitable organic builders include the alkali metal, ammonium and substituted ammonium, citrates, succinates, malonates, fatty acid sulfonates, carboxymethoxy succinates, ammonium polyacetates, carboxylates, polycarboxylates, aminopolycarboxylates, polyacetyl carboxylates and polyhydroxysulfonates.

Other suitable organic builders include the higher molecular weight polymers and co-polymers known to have builder properties, for example appropriate polyacrylic acid, polymaleic and polyacrylic/polymaleic acid copolymers and their salts.

The dishwashing detergent composition may contain bleaching agents of the chlorine/bromine-type or the oxygen-type. Examples of inorganic chlorine/bromine-type bleaches are lithium, sodium or calcium hypochlorite and hypobromite as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds are also suitable.

The oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED and glycerol triacetate.

The dishwashing detergent composition of the invention may be stabilized using conventional stabilizing agents for the enzyme(s), e.g. a polyol such as e.g. propylene glycol, a sugar or a sugar alcohol, lactic acid, boric acid, or a boric acid derivative, e.g. an aromatic borate ester.

The dishwashing detergent composition of the invention may also contain other conventional detergent ingredients, e.g. deflocculant material, filler material, foam depressors, and-corrosion agents, soil-suspending agents, sequestering agents, anti-soil redeposition agents, dehydrating agents, dyes, bactericides, fluorescers, thickeners and perfumes.

Finally, the α-amylase variants of the invention may alone or in combination with at least one amylolytic enzyme, e.g. one of those defined above, be used in conventional dishwashing detergents, e.g. any of the detergents described in any of the following patent publications: EP 551670, EP 533239, WO 9303129, EP 507404, U.S. Pat. No. 5,141,664, GB 2247025, EP 414285, GB 2234980, EP 408278, GB 2228945, GB 2228944, EP 387063, EP 385521, EP 373851, EP 364260, EP 349314, EP 331370, EP 318279, EP 318204, GB 2204319, EP 266904, U.S. Pat. No. 5,213,706, EP 530870, CA 2006687, EP 481547, EP 337760, WO 93/14183, U.S. Pat. No. 5,223,179, WO 93/06202, WO 93/05132, WO 92/19707, WO 92/09680, WO 92/08777, WO 92/06161, WO 92/06157, WO 92/106156, WO 91/13959, EP 399752, U.S. Pat. No. 4,941,988, U.S. Pat. No. 4,908,148.

Textile desizing In the textile processing industry, α-amylases are traditionally used as auxiliaries in the desizing process to facilitate the removal of starch-containing size which has served as a protective coating on weft yarns during weaving.

Complete removal of the size coating after weaving is important to ensure optimum results in the subsequent processes, in which the fabric is scoured, bleached and dyed. Enzymatic starch break-down is preferred because it does not involve any harmful effect on the fibre material.

In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional α-amylases are not very compatible with high pH levels and bleaching agents. The non-enzymatic breakdown of the starch size does lead to some fibre damage because of the rather aggressive chemicals used.

Accordingly, it would be desirable to use α-amylase enzymes having an improved resistance towards or compatible with oxidation (bleaching) agents at elevated pH, in order to retain the advantages of enzymatic size break down in a time-saving simultaneous desizing/scouring/bleaching process.

It is contemplated that α-amylase variants of the invention may be found to have an improved resistance towards oxidation agents and thus be useful in desizing processes as described above, in particular for substitution of non-enzymatic alkali or oxidation agents used today.

Figure 1B:
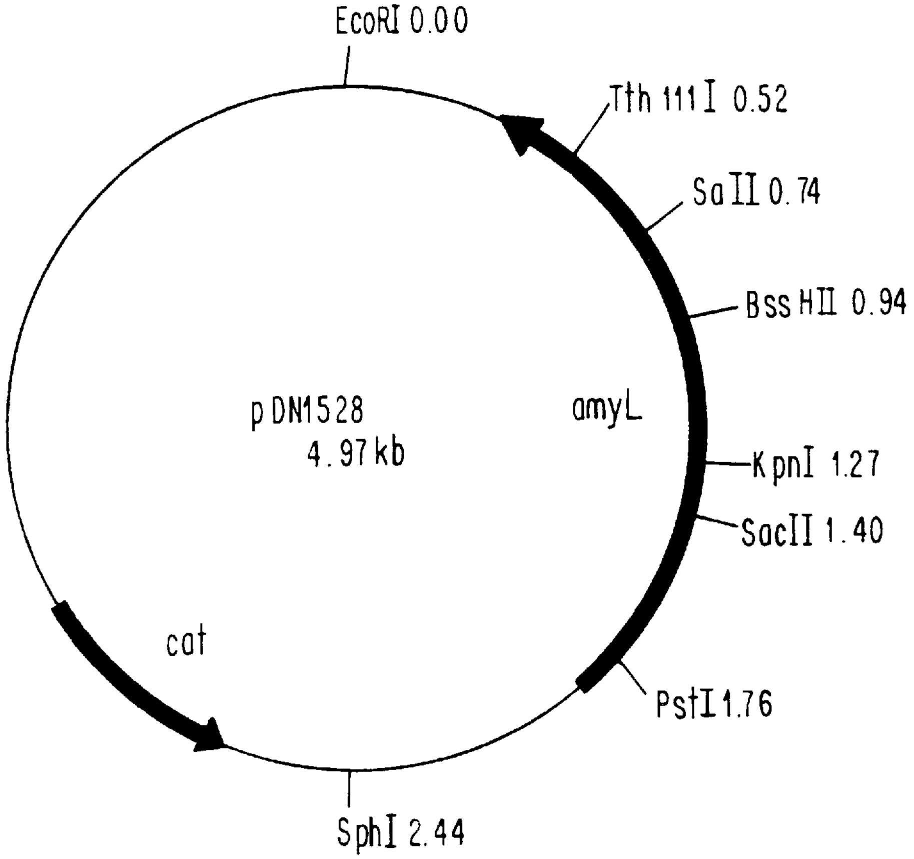
Figure 2:
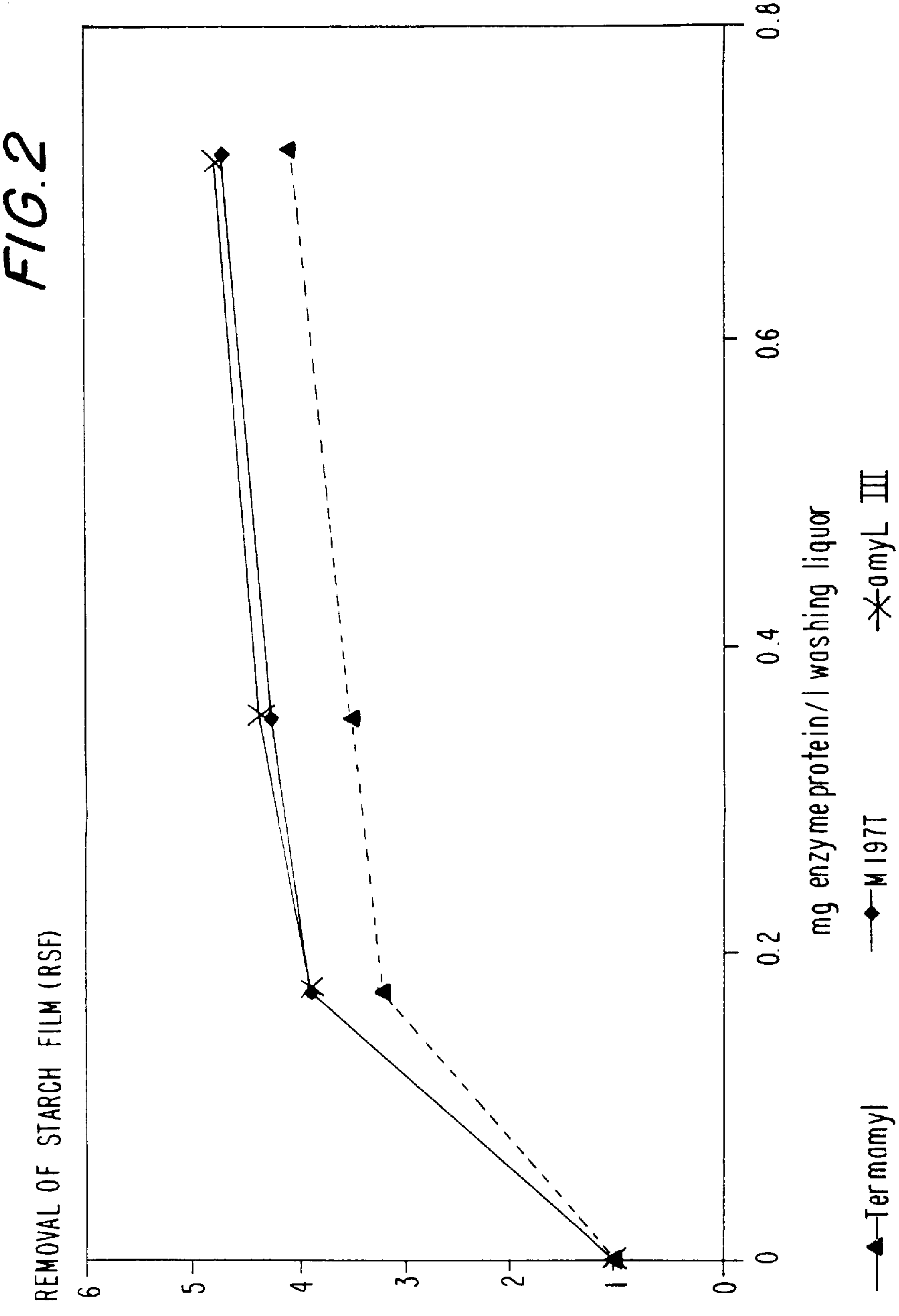
Figure 3:
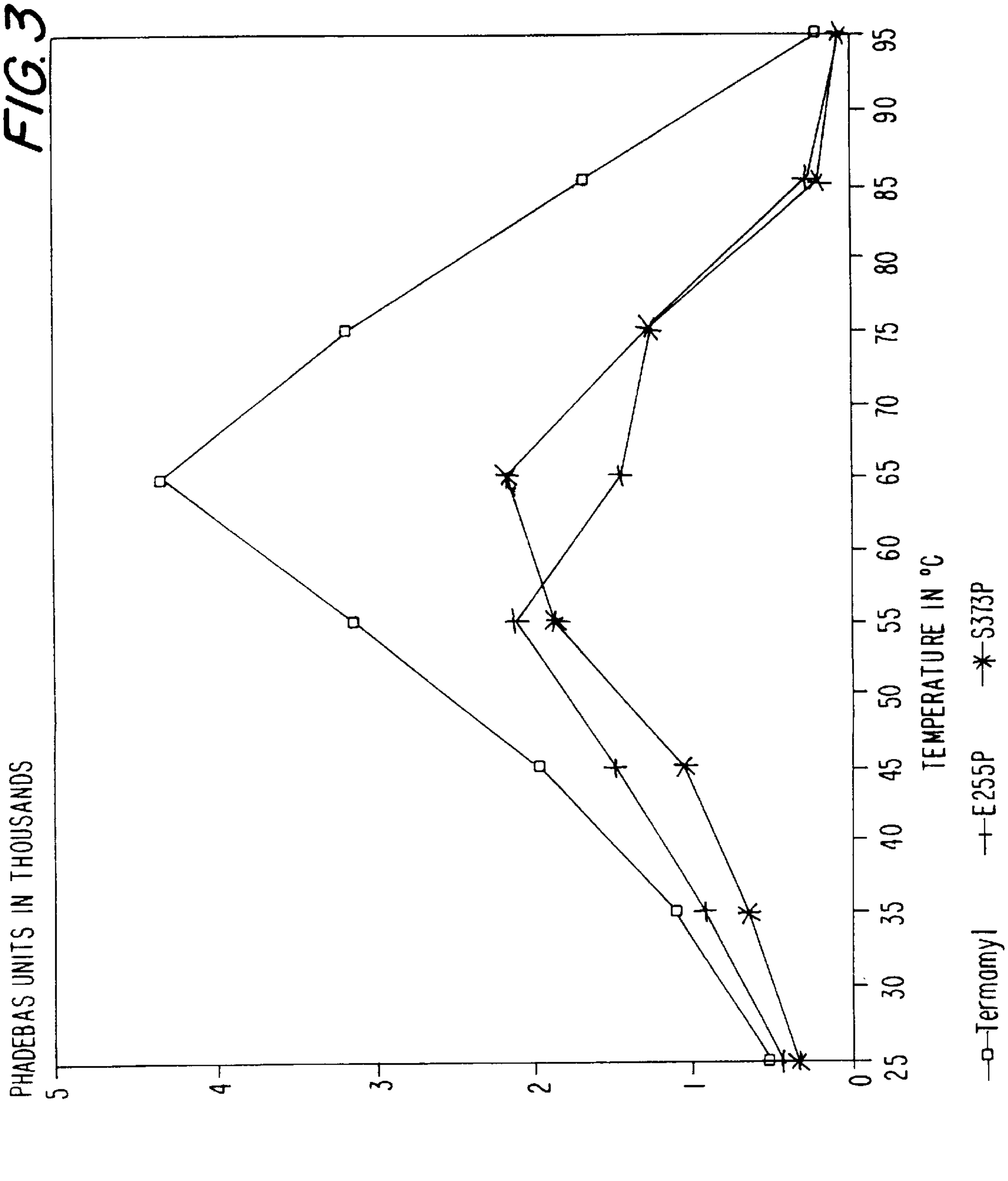

The present invention is further described with reference to the appended drawing in which FIG. 1A is a restriction map of plasmid pDN1380, FIG. 1B a restriction map of plasmid pDN1528, FIG. 2 is a graph showing the improved dishwashing performance of M197T and amyL variant III compared to the parent α-amylase when tested at pH 10.5 and 55° C., FIG. 3 is a graph showing the temperature/activity profile of Termamyl® compared to E255P and S373P in an automatic dishwashing detergent (5 g/l) (pH 10.1) as a function of the temperature (0.41 Phadebas Units=1 NU).

Figure 4:
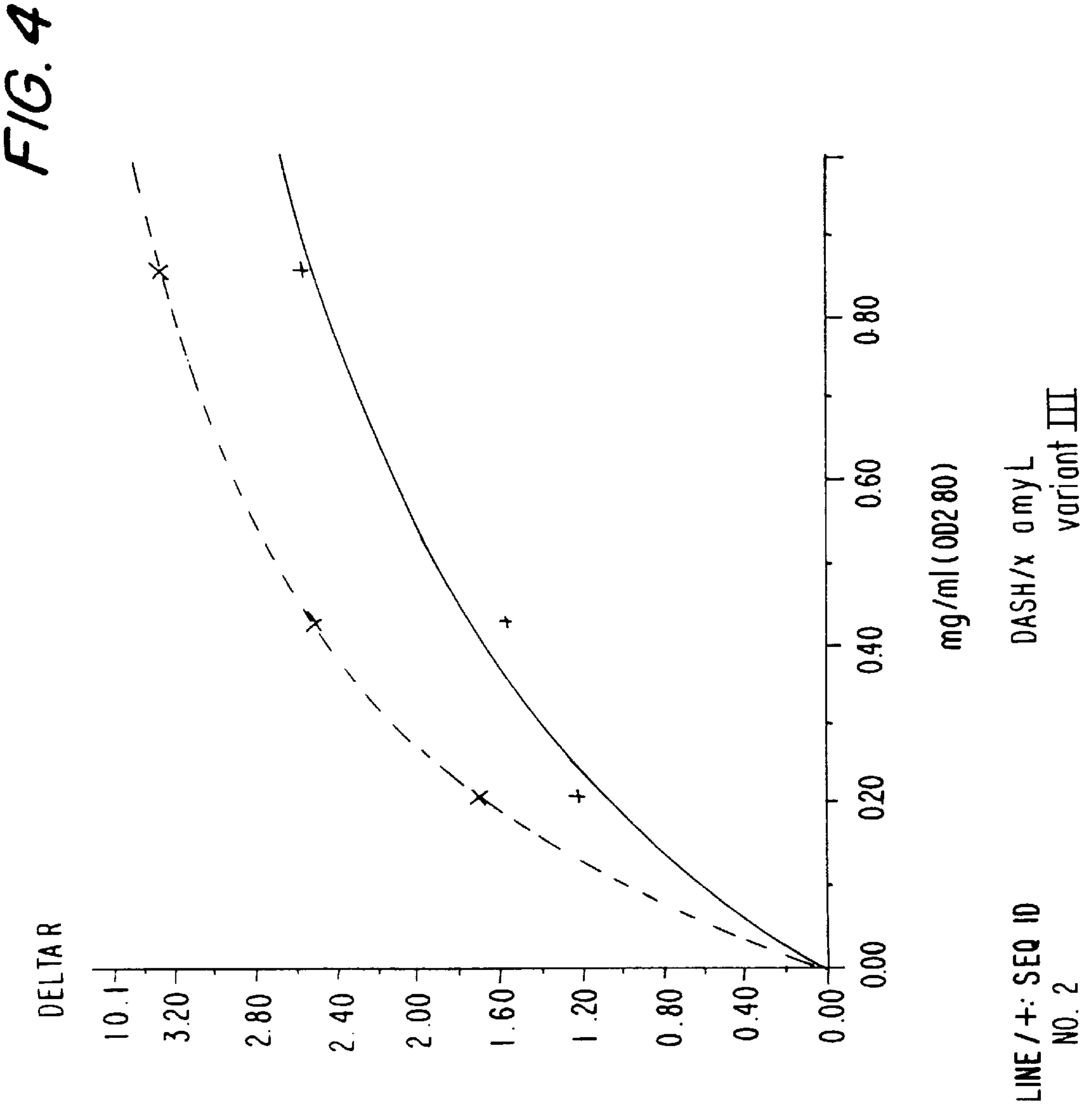
Figure 5:
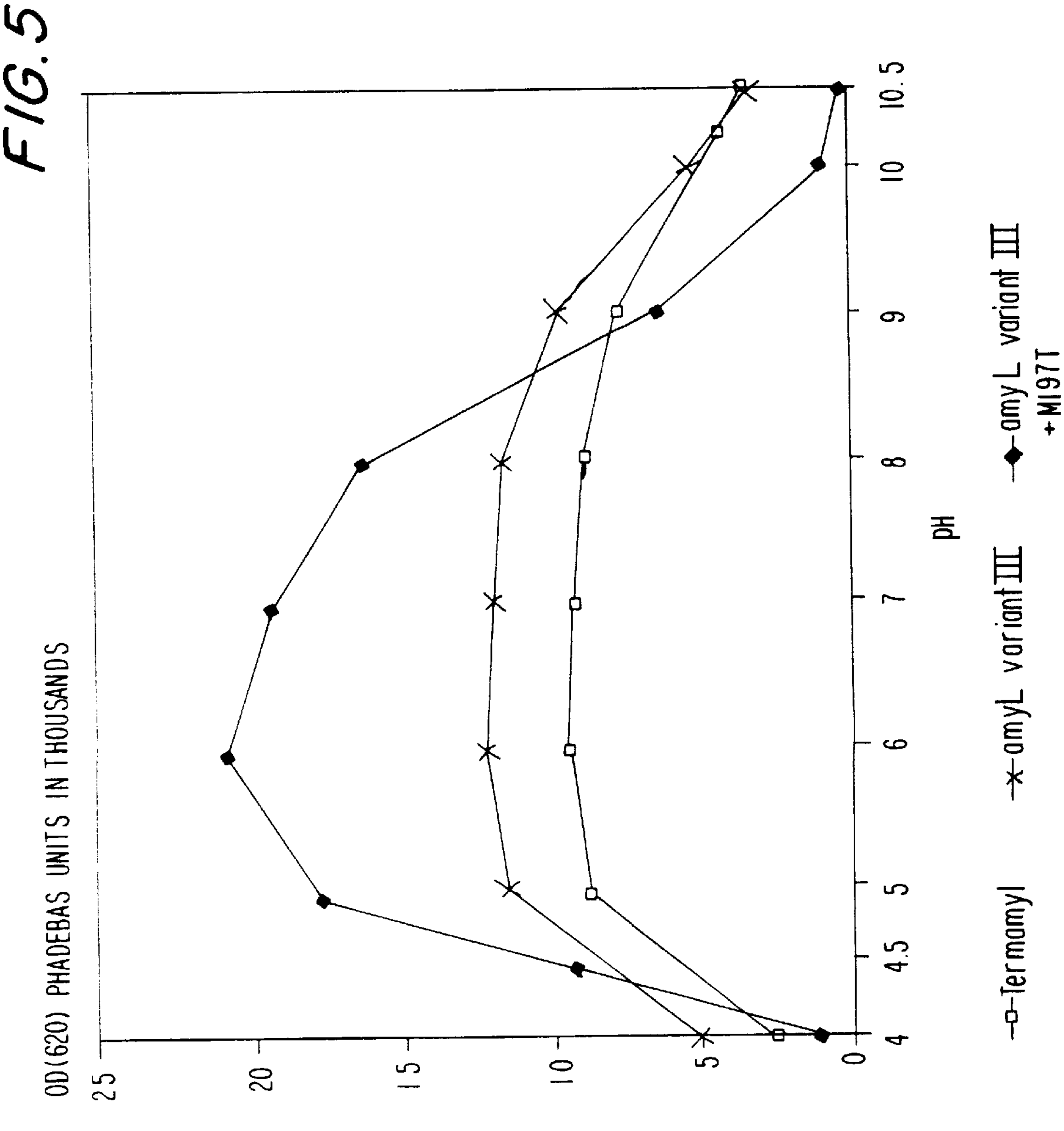
Figure 6:
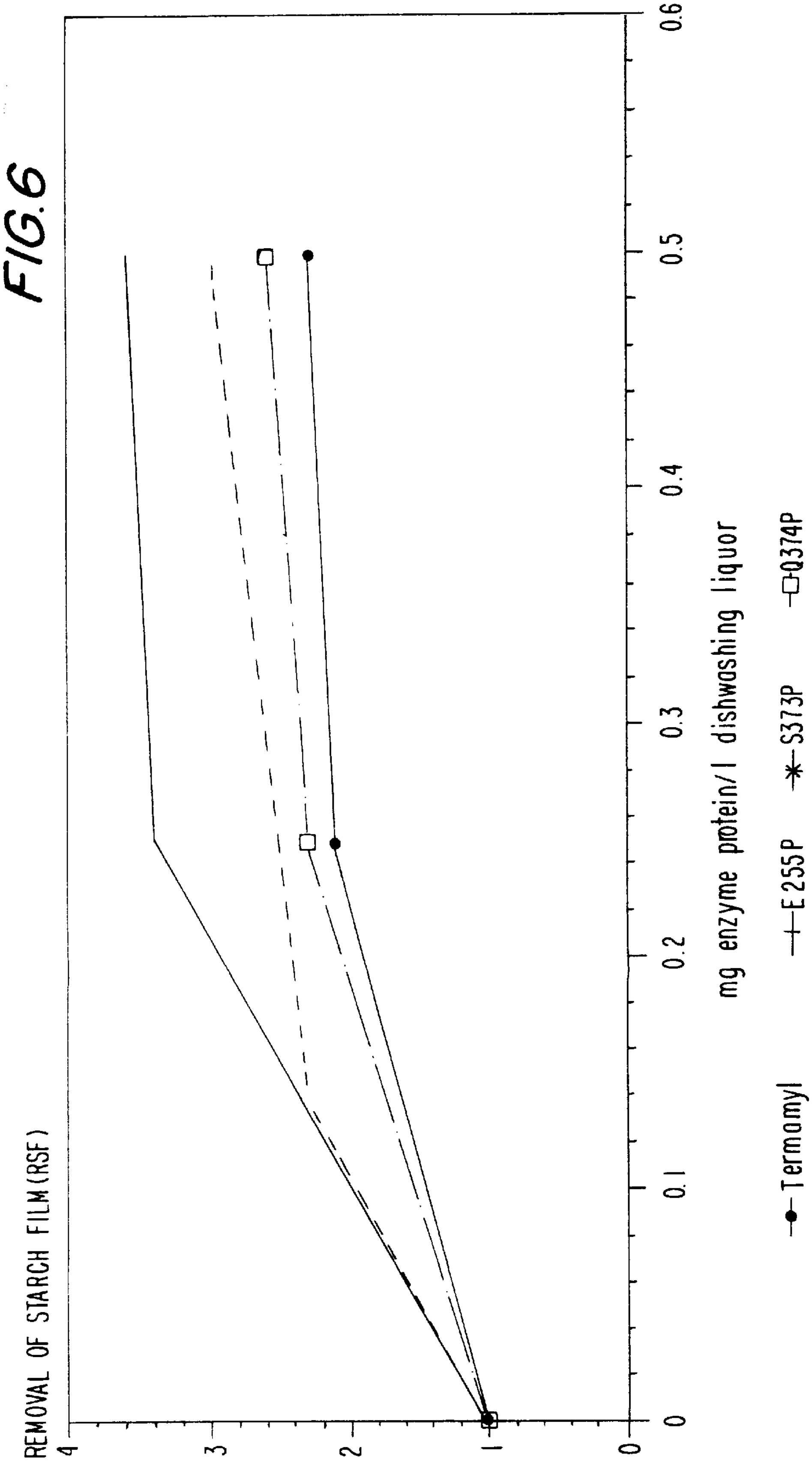
Figure 7:
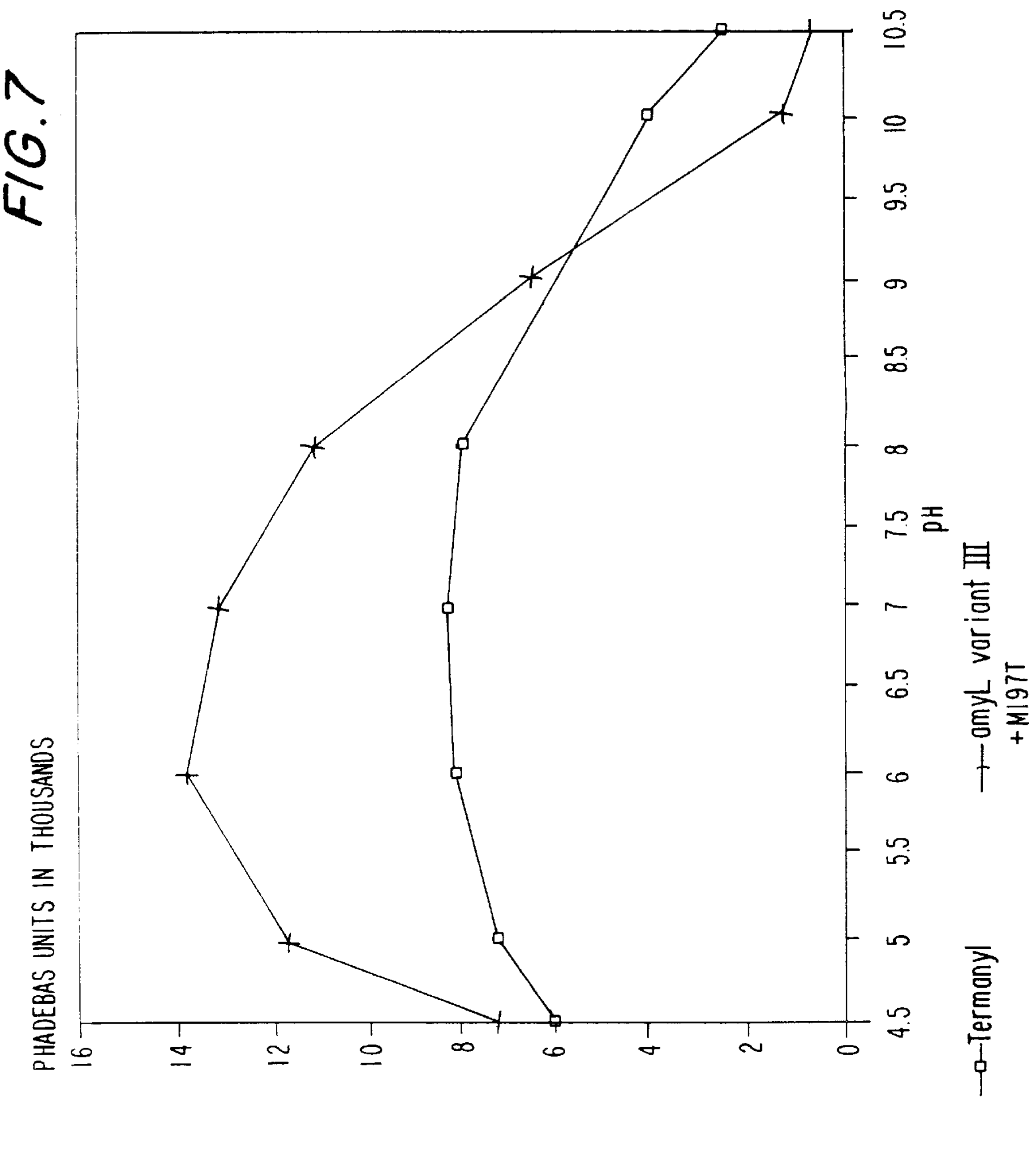
Figure 8:
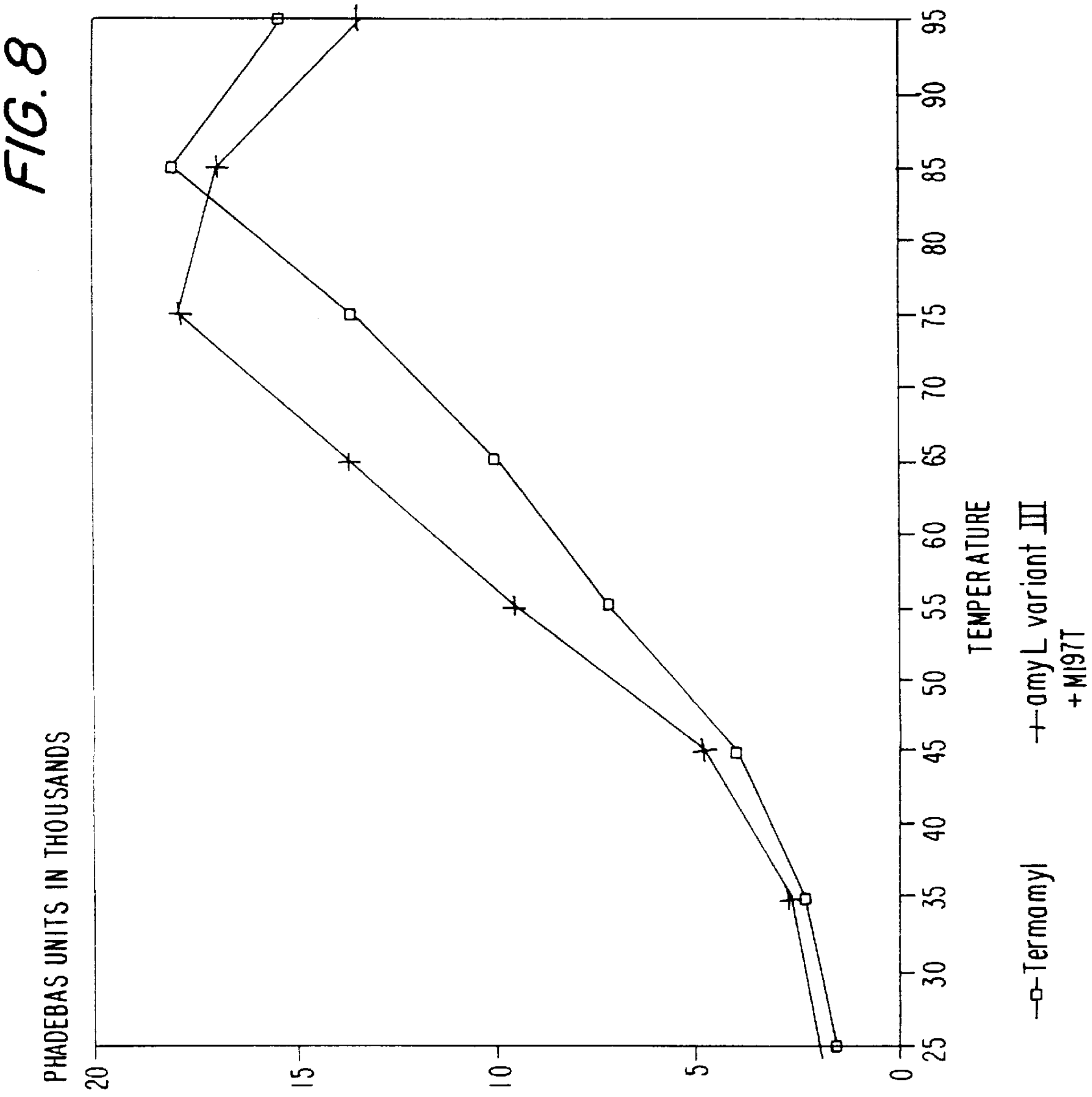
Figure 9:
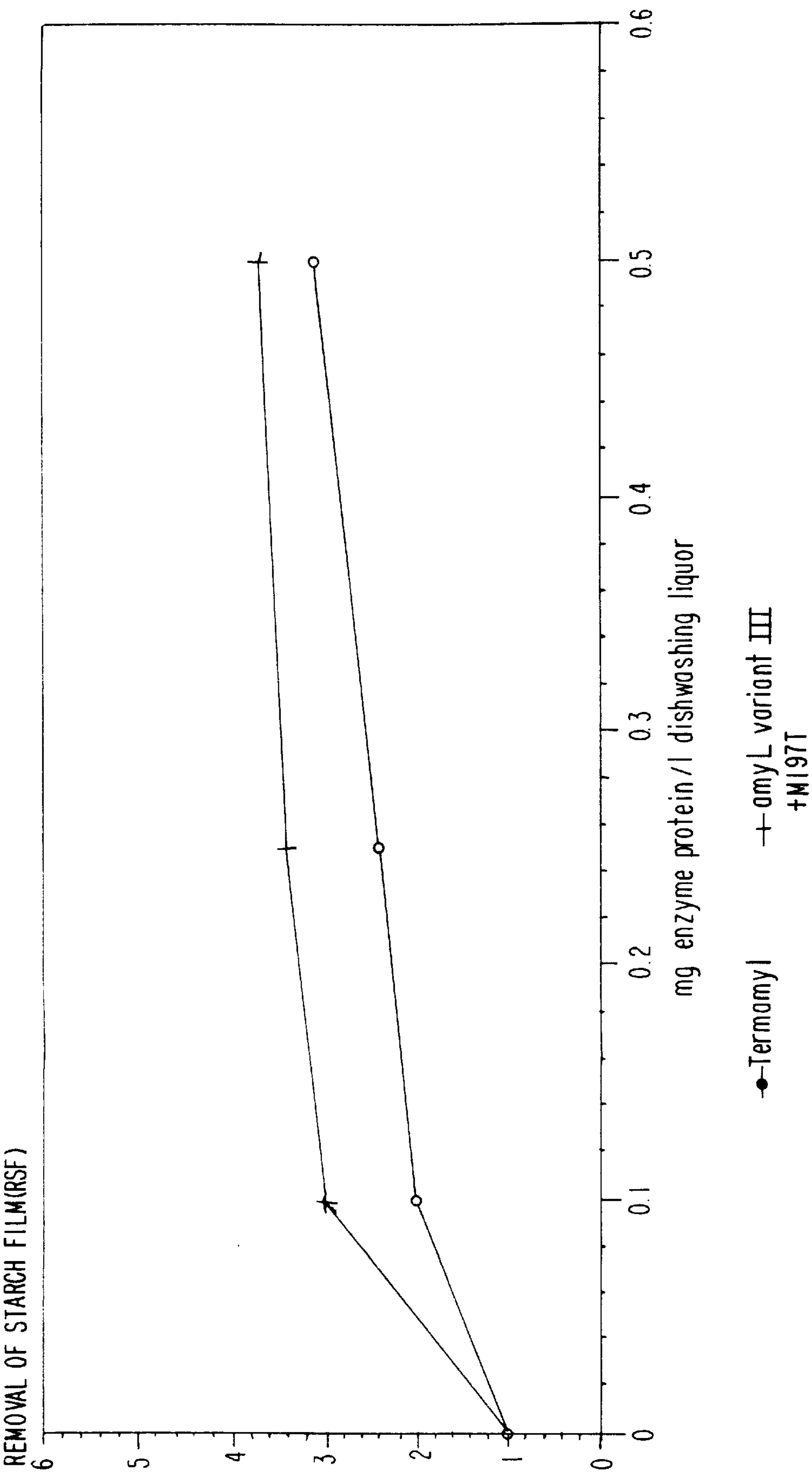
Figure 10:
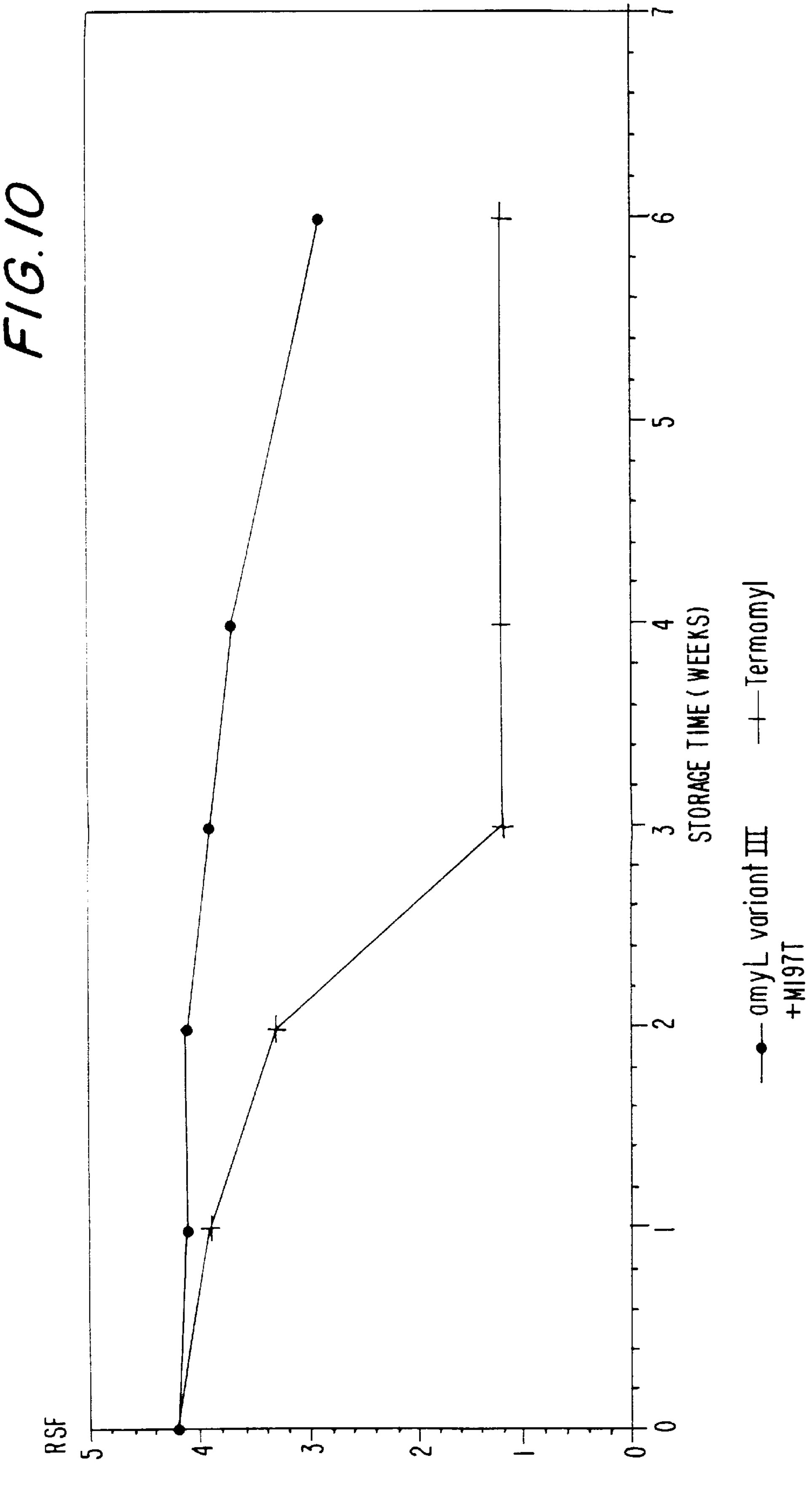
Figure 11:
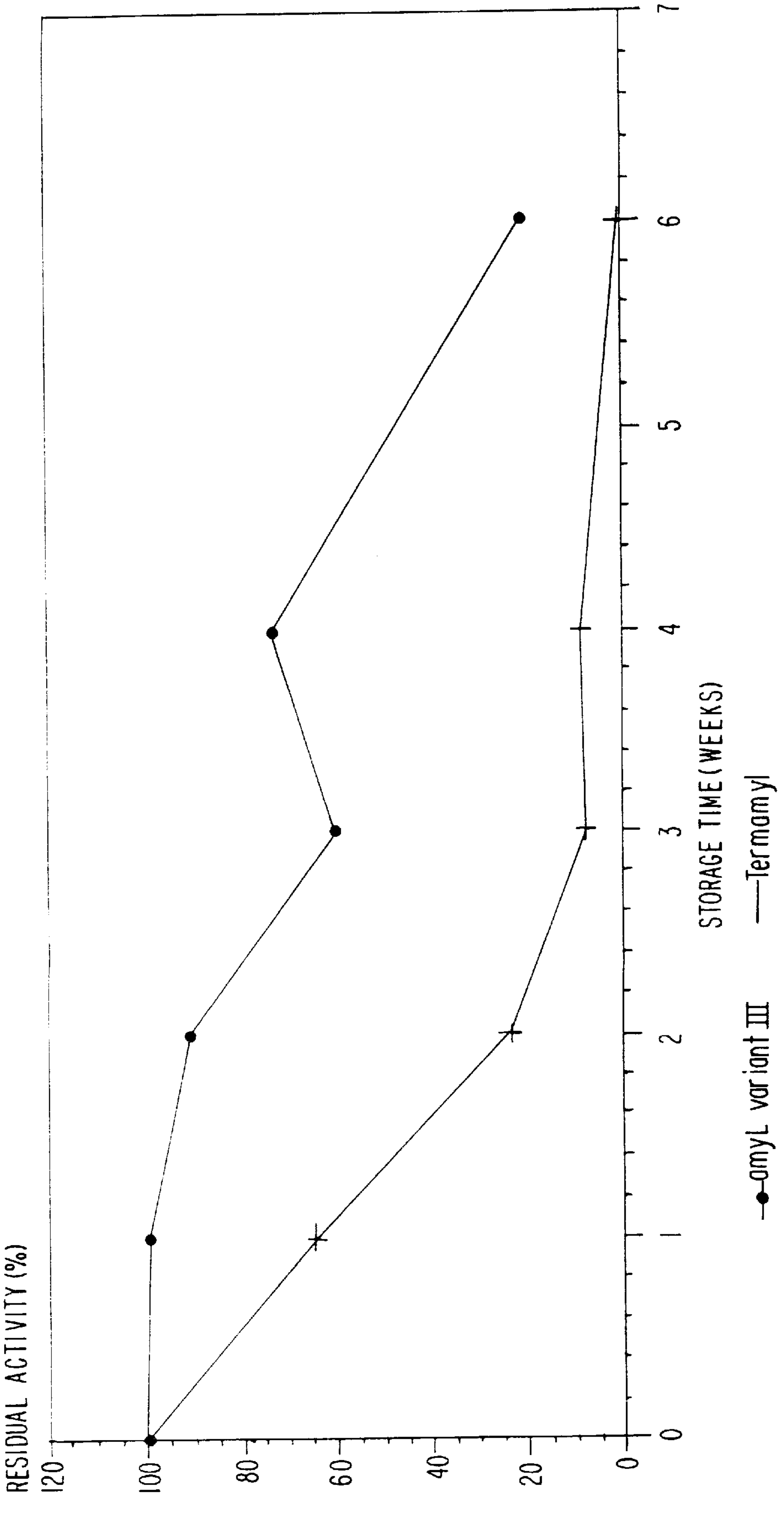

FIG. 4 shows the delta reflection for different concentrations of enzyme obtained during laundry washing as described in Example 8. The delta reflection has been calculated from the reflection obtained for a swatch having been washed with the relevant enzyme and the reflectance obtained for a swatch washed without enzyme, FIG. 5 shows the pH/activity profiles (activity/mg enzyme) of the amyL variant III and the amyL variant III+M197T of the invention as compared to that of Termamyl® measured at 60° C., FIG. 6 is a graph showing the performance dose/response curves of E255P, S373P and Q374P compared to Termamyl® in full-scale dishwash performance evaluation (55° C., 4 g/l of standard European-type automatic dishwashing detergent), FIG. 7 shows the temperature/activity profile of amyL variant III+M197T compared to Termamyl® according to mg enzyme (50mM Britton-Robinson buffer, 0.1 mM $CaCl_2$, 55° C.), FIG. 8 shows the temperature/activity profile of the amyL variant III+M197T of the invention compared to Termamyl® (pH 9.0, 100 mM Glycine buffer, 0.1 mM $CaCl_2$), FIG. 9 shows the dishwashing performance of the amyL variant III+M197T of the invention compared to Termamyl® (pH 10.3, 4 g/l of a standard European-type automatic dishwashing detergent), and FIGS. 10 and 11 show the results obtained following storage in a standard European-type automatic dishwashing detergent at 30° C./60 r.h. of amyL variant III+M197T compared to Termamyl® in a detergent composition.

The following examples further illustrate the present invention, and they are not intended to be in any way limiting to the scope of the invention as claimed.

MATERIALS AND METHODS

Determination of α-amylase activity

60 -Amylase activity is given herein in terms of Novo Units (NU). One thousand NU [i.e. one Kilo Novo α-amylase Unit (KNU)] is the amount of enzyme which, per hour, under standard conditions (37±0.05° C.; Ca content 0.0003 M; pH 5.6) dextrinizes 5.26 grams of starch dry substance (Merck Amylum solubile, Erg. B.6 Batch No. 9947275). Further details concerning the definition of NU are given in a brochure ("AF 9/6") which is available from Novo Nordisk A/S, Novo Allé, DK-2880 Bagsvaerd, Denmark.

The determination of α-amylase activity is performed by a method—developed by Novo Nordisk A/S for determination of Termamyl® activity—in which Phadebas tablets (Phadebas® Amylase Test, supplied by Pharmacia Diagnostics) are used as substrate. This substrate is a cross-linked insoluble blue-colored starch polymer which is mixed with bovine serum albumin and a buffer substance and tabletted. After suspension in water, the starch is hydrolyzed by the α-amylase giving soluble blue fragments. The absorbance of the resulting blue solution, measured at 620 nm, is a function of the α-amylase activity; the enzyme activity is compared to that of an enzyme standard. Standard conditions for the method are:

Temperature: 37° C. pH: 7.3 Reaction time: 15 minutes

Calcium: 0.15 nM

Further details concerning this method are given in a brochure ("AF 207/1") which is available from Novo Nordisk A/S, Novo Allé, DK-2880 Bagsvaerd, Denmark.

Somogyi Method for the Determination of Reducing Sugars

The method is based on the principle that the sugar reduces cupric ions to cuprous oxide which reacts with arsenate molybdate reagent to produce a blue color which is measured spectrophotometrically. The solution which is to be examined must contain between 50 and 600 mg of glucose per liter.

1 ml of sugar solution is mixed with 1 ml of copper reagent and placed in a boiling water bath for 20 minutes. The resulting mixture is cooled and admixed with 1 ml of Nelson's color reagent and 10 ml of deionized water. The absorbency at 520 nm is measured.

In the region 0–2 the absorbance is proportional to the amount of sugar, which may thus be calculated as follows:

$$\text{mg glucose/1} = \frac{100\ (\text{sample} - \text{blank})}{(\text{standard} - \text{blank})}$$

$$\%\ \text{glucose} = \frac{(\text{sample} - \text{blank})}{100\ (\text{standard} - \text{blank})}$$

REAGENTS

1. Somogyi's copper reagent 35.1 g of $Na_2HPO_4.2H_2O$, and 40.0 g of potassium sodium tartate ($KNaC_4H_4O_2.4H_2O$) are dissolved in 700 ml of deionized water.

100 ml of 1N sodium hydroxide and 80 ml of 10% cupric sulphate ($CuSO_4.5H_2O$) are added, 180 g of anhydrous sodium sulphate are dissolved in the mixture, and the volume is brought to 1 liter with deionized water.

2. Nelson's color reagent 50 g of ammonium molybdate are dissolved in 900 ml of deionized water. Then 42 ml of concentrated sulphuric acid (Merck) are added, followed by 6 g of disodium hydrogen arsenate heptahydrate dissolved in 50 ml of deionized water, and the volume is brought to 1 liter with deionized water.

The solution must stand for 24–48 hours at 37° C. before use. It must be stored in the dark in a brown glass bottle with a glass stopper.

3. Standard 100 mg of glucose (May & Baker, anhydrous) are dissolved in 1 liter of deionized water.

Reference: J. Biol. Chem. 153, 375 (1944)

Determination of Km

The kinetics of hydrolysis catalyzed by the amylases at various substrate concentrations were determined using the Somogyi-Nelson method with soluble starch as substrate (Merck 1252.). The hydrolysis velocities were measured under different substrate concentrations (1%, 0.5%, 0.3%, 0.25% and 0,2% starch solution). The number of reducing sugars were measured using the Somogyi-Nelson method, and determined as glucose eqv. made/mg of amylase x h giving the hydrolysis velocity. The data were plotted according to the Michaelis-Menten and Lineweaver-Burk equations. From these equations Vmax and Km can easily be calculated.

Laundry washing

Detergent: Commercial European heavy duty liquid compact detergent (HDL)

Detergent dosage: 5 g/l

Soil: Potato starch colored with Cibacron Blue 3GA

Water hardness: 18° dH

Time: 20 minutes pH (during wash): approx. 7.8

Evaluation: Reflectance at 660 nm.

Automatic dishwashing

1) Washing conditions

Amylases: *B. licheniformis* α-amylase (SEQ ID No.2)
M 197T
QL37

Amylase dosage: 0–0.72 mg enzyme protein/l washing liquor

Detergent: standard European-type automatic dishwashing detergent

Detergent dosage: 4.2 g/l washing liquor

Soil: Corn starch on plates and glasses

Dishwashing: 55° C. program, Bauckenecht GS 1272 pH: 10.3 during dishwashing

2) Evaluation

Removal of starch film (RSF) from plates and glasses is evaluated after coloring with iodine on the following scale from 0 to 6:

| Rating | Dishware | Glassware6 | clean | clean |
|---|---|---|---|---|
| 5 | spots | thin | | |
| 4 | thin | moderate | | |
| 3 | moderate | heavy | | |
| 2 | heavy | very heavy | | |
| 1 | very heavy | extremely heavy | | |
| 0 | blind (unwashed) | blind (unwashed) | | |

Mini dishwashing assay

A suspension of starchy material is boiled and cooled to 20° C. The cooled starch suspension is applied on small, individually identified glass plates (approx. 2×2 cm) and dried at a temperature in the range of 60°–140° C. in a drying cabinet. The individual plates are then weighed. For assay purposes, a solution of standard European-type automatic dishwashing detergent (5 g/l) having a temperature of 55° C. is prepared. The detergent is allowed a dissolution time of 1 minute, after which the amylase variant in question is added to the detergent solution (contained in a beaker equipped with magnetic stirring) so as to give an enzyme concentration of 0.5 mg/ml. At the same time, the weighed glass plates, held in small supporting clamps, are immersed in a substantially vertical position in the amylase/detergent solution, which is then stirred for 15 minutes at 55° C. The glass plates are then removed from the amylase/detergent solution, rinsed with distilled water, dried at 60° C. in a drying cabinet and re-weighed. The performance of the amylase variant in question [expressed as an index relative to Termamyl® (index 100)] is then determined from the difference in weight of the glass plates before and after treatment, as follows:

$$\text{Index} = \frac{\text{weight loss for plate treated with } \alpha\text{-amylase variant}}{\text{weight loss for plate treated with Termamyl}^{®}} \cdot 100$$

EXAMPLES

Example 1

In this example the construction of DNA encoding a number of different *B. licheniformis* variants are described. Each variant is referred to by its amino acid modifications compared to the parent *B. licheniformis* α-amylase.

Plasmid pDN1528 (FIG. 1B) has been used for these constructions. The plasmid is a derivative of the *B. subtilis* plasmid pUB110 (Gryczan et al., 1978) and contains the pUB110 origin of replication, the cat gene conferring chloramphenicol resistance, and the gene encoding the *B licheniformis* α-amylase having the DNA sequence shown in SEQ ID No. 1 (=amyL). The *B. licheniformis* α-amylase promoter (amyL promoter) transcribes the amyL gene.

Construction of amyL variant I: (1–2)*+L3V

The deletion of residues 1 and 2, and the substitution of leucine 3 with a valine were introduced simultaneously in amyL by PCR amplification of a fragment of DNA using the amyL gene (located on plasmid pDN1528) as a template and two oligonucleotides as primers. The 5'primer #6079 covers the region of residues 1–3 and the unique Pstl restriction site. The sequence of this primer is given in Table 1:

The other primer 1C (Table 1) is located 3' to the mutagenic primer and has a sequence identical to amyL.

PCR was carried out as 30 cycles of (30 seconds at 94° C., 30 seconds at 50° C., and 60 seconds at 73° C.) followed by 600 seconds at 73° C.

The amplified DNA fragment was purified and digested with restriction enzymes Pstl and SacII. The resulting Pstl-SacII DNA fragment was ligated with plasmid pDN1528 digested with the same unique restriction enzymes. The resulting plasmid carries a variant amyL gene with the desired mutations, and the variant protein can be expressed from this construct.

Construction of amyl variant II: (1–2)*+L3V+M15T

The substitution of methionine 15 with a threonine was carried out by overlap-extension mutagenesis (Higuchi et al., 1988) using the amyL variant ((1–2)*+L3V) as a template and the mutagenic primers #6164 and #6173 listed in Table 1. Thus, the resulting gene contains the deletion of residues 1 and 2, L3V and M15T.

In a PCR reaction (reaction A) a 480 bp DNA fragment was amplified by the use of two DNA primers, viz. #6164 containing the desired nucleotide alterations (Table 1) and one flanking primer, 1C. A separate PCR reaction (reaction B) amplified a 140 bp DNA fragment to the opposite site of the mutation site by the use of primer 1B and primer #6173. These PCR reactions were 25 cycles of (30 seconds at 94° C., 30 seconds at 50° C., and 60 seconds at 73° C.) followed by 600 seconds at 73° C. The amplified fragments from reactions A and B overlap around the mutation site and a longer fragment of DNA was amplified in a third PCR reaction C: 20 cycles of (30 seconds at 94° C., 30 seconds at 50° C., and 60 seconds at 73° C.) followed by 600 seconds at 73° C., by the use of only the two flanking primers, 1B and 1C. Reaction C DNA was digested with Pstl and SacII restriction endoneucleases, and the resulting 360 bp PstI-SacII DNA fragment was subcloned into plasmid pDN1528, digested with the same unique restriction enzymes.

Construction of amyL variant III: (1–2)*+L3V+M15T+R23K+S29A+A30E+Y31H+A33S+E34D+H35I A) By site-specific mutagenesis In the DNA sequence encoding the amyL variant II ((1–2)*+L3V+M15T) constructed as described above, the following amino acid substitutions were introduced simultaneously: R23K, S29A, A30E, Y31H, A33S, E34D, and H35I by the overlap extension method as previously described.

Primers 1C and Reg 1A were used in reaction A, and primers 1B and Reg 1B were used in reaction B. The conditions for the PCR reactions were identical to those described above, and a PCR reaction C was carried out in a similar way. All the mutations were cloned on the 360 bp PstI-SacII fragment into pDN1528 as mentioned above.

This amyL variant may be prepared by the following alternative method:

B) Preparation of amyL variant III by α-amylase gene fission

The plasmids useful for carrying out gene fusions are very similar and are all based on the Bacillus expression vector, pDN1380 (cf. FIG. 1A).

pDN1380 contains an origin of replication from plasmid pUB110, the maltogenic α-amylase promoter (P-beta promoter) described by Diderichsen and Christiansen (1988) located in front of a polylinker, and the cat gene encoding chloramphenicol acetyl transferase from the cloning vector pC194 (see, e.g., Erlich, 1977).

Amylase encoding genes should be cloned in pDN1380 in such a way that the amylase gene is transcribed from the P-beta promoter. A resulting plasmid pDN1681 containing the *B. amyloliquefaciens* α-amylase gene having the DNA sequence shown in SEQ ID No. 3 (amyQ), a plasmid pDN1750 containing the *B. stearothermophilus* α-amylase gene having the DNA sequence shown in SEQ ID No. 5 (amyS) and a plasmid pDN1700 containing the *B. licheniformis* α-amylase gene having the DNA sequence shown in SEQ ID No. 1 (amyL) may be obtained.

Primers:

pUB110ori: 5' CACTTCAACGCACCTTTCAGC 3' (SEQ ID No: 8)

catl: 5' CATGGACTTCATTTACTGGG 3' (SEQ ID No. 9)

QA: 5' CACTGCCGTCTGGATTCCCC 3' (SEQ ID No: 10)

QB: 5' GGGAATCCAGACGGCAGTG 3' (SEQ ID No: 11)

SA: 5' GAATTCAATCAAAAAGGGACGGTTCGG 3' (SEQ ID No: 12)

SB: 5' CCGTCCCTTTTTGATTGAATTCGCC 3' (SEQ ID No: 13)

The amylase gene fusions may be constructed by the PCR overlap-extension method as described by Higuchi et al. 1988.

The Polymerase Chain Reaction (PCR) may be used to amplify the fragment of pDN1681 (5'-end of the amyQ) located between primer QB and pUB110ori (reation A). In a separate PCR (reaction B), the 3'-end of amyL may be amplified as the fragment between primer QA and primer cat1 in plasmid pDN1700. The two purified fragments may be used in a third PCR (reaction C) in the presence of the primers flanking the total region, i.e. pUB110ori and cat1.

The fragment amplified in the third reaction may be purified, digested with restriction endonucleases EcoRI and SphI and ligated with the 2.6 kb fragment obtained from plasmid pDN1380 by a digestion with restriction endonucleases EcoRI and SphI. A protease-and amylase-weak *B. subtilis* strain (e.g. strain SHA273 mentioned in WO 92/11357) may be transformed with the ligated plasmids, starch degrading transformants may be selected on starch-containing agarose plates and the amplified DNA sequence may be verified.

Polymerase Chain Reactions may be carried out under standard conditions, as described by Higuchi et al. 1988.

Reaction A and B are 15 cycles of (60 seconds at 94° C., 60 seconds at 45° C., and 90 seconds at 73° C.) followed by 600 seconds at 73° C. Reaction C is 15 cycles of (60 seconds at 94° C., 60 seconds at 50° C., and 90 seconds at 73° C.) followed by 600 seconds 73° C.

The amino acid sequence in the mature protein from the construct described in Example B) is identical to the sequence of the mature protein from Example A), but the DNA sequences are different in the 5' end of the genes. Furthermore, the construct in Example A) has the amyL signal sequence whereas the construct B) has the signal sequence of the *B. amyloliquefaciens* α-amylase.

Example 2

The amyL variant III prepared as described in A) or B) in Example 1 above and the site-specific mutation M197T were combined by subcloning a KpnI-SalI fragment containing M197T into the DNA sequence encoding amyL variant III ((1–2)*+L3V+M15T+R23K+S29A+A30E+Y31H+A33S+E34D+H35I) described above.

KpnI and SalI are unique restriction sites found in the *B. licheniformis* α-amylase encoding sequence and the KpnI-SalI fragment constitutes a 534 bp fragment containing the M197T mutation prepared by Nelson and Long mutagenesis as described in WO 94/02597. The same sites, KpnI and SalI, are also unique in the *B. licheniformis* α-amylase variant III described above and therefore the 534 bp fragment can be cloned directly into the vector fragment KpnI/SalI obtained from amyL variant III. The resulting DNA encodes amyL variant III with the additional mutation M197T.

In an alternative method, the M197T mutation may be introduced in the *B. licheniformis* α-amylase encoding DNA sequence SEQ ID No. 1 by the method described by Nelson and Long (1981) and further exemplified in WO 94/02597 with the following sequences of the mutagenic primer 5'-CGGCATACGTCAAATAATCATAGTTGC-3' (SEQ ID No: 14)

where the underlined nucleotide introduce the mutation M197T.

Example 3

A number of other mutations were introduced in the DNA sequence shown in SEQ ID No. 1 encoding the *B. licheniformis* α-amylase by similar methods, using the oligonucleotides listed in Table 1 below. Combinations of mutations were done by subcloning, if possible, or by mutagenesis carried out on a Termamyl® variant template.

E255P was constructed by the method described by Higuchi et al., 1988:

template: amyL in pDN1528.

PCR A: primers E255P,A and 2C. Standard conditions: 25 cycles of (30 seconds at 94° C., 30 seconds at 50° C., and 60 seconds at 73° C.) followed by 600 seconds at 73° C.

PCR B: primers E255P,B and 2B. Standard conditions.

PCR C: standard C reaction: 20 cycles of (30 seconds at 94° C., 30 seconds at 50° C., and 60 seconds at 73° C.) followed by 600 seconds at 73° C.

The mutation was subcloned as a 330 bp Kpnl-BssHII fragment into pDN1528.

T341P was constructed similarly to amyL variant I. One PCR reaction was carried out on amyL variant III by the use of primers T341P and 3C. A 210 bp SalI-Tth111I fragment was subcloned into pDN1528.

S373P was constructed by the method described by Higuchi et al., 1988:

template: amyL in pDN1528.

PCR A: primers S373P,A and 3C. Standard conditions: 25 cycles of (30 seconds at 94° C., 30 seconds at 50° C., and 60 seconds at 73° C.) followed by 600 seconds at 73° C.

PCR B: primers S373,B and 3B. Standard conditions.

PCR C: standard C reaction: 20 cycles of (30 seconds at 94° C., 30 seconds at 50° C., and 60 seconds at 73° C.) followed by 600 seconds at 73° C.

The mutation was subcloned as a 210 bp SalI-Tth111I fragment into pDN1528.

O374P was constructed by the method described by Higuchi et al., 1988:

template: amyL in pDN1528.

PCR A: primers Q374P,A and 3C. Standard conditions: 25 cycles of (30 seconds at 94° C., 30 seconds at 50° C., and 60 seconds at 73° C.) followed by 600 seconds at 73° C.

PCR B: primers Q374P,B and 3B. Standard conditions.

PCR C: standard C reaction: 20 cycles of (30 seconds at 94° C., 30 seconds at 50° C., and 60 seconds at 73° C.) followed by 600 seconds at 73° C.

The mutation was subcloned as a 210 bp SalI-Tth111I fragment into pDN1528.

S148N was constructed by the method described by Higuchi et al., 1988:

template: amyl in pDN1528.

PCR A: primers S148N,A and 2C. Standard conditions: 25 cycles of (30 seconds at 94° C., 30 seconds at 50° C., and 60 seconds at 73° C.) followed by 600 seconds at 73° C.

PCR B: primers S148N,B and 1B. Standard conditions as above

PCR C: standard C reaction: 20 cycles of (30 seconds at 94° C., 30 seconds at 50° C., and 60 seconds at 73° C.) followed by 600 seconds at 73° C.

The mutation was subcloned as a 120 bp Kpnl-Sacll fragment into pDN1528.

L230I,V233A was constructed by the method described by Higuchi et al., 1988:

template: amyL in pDN1528.

PCR A: primers L230I+V233A, A and 2C. Standard conditions: 25 cycles of (30 seconds at 94° C., 30 seconds at 50° C., and 60 seconds at 73° C.) followed by 600 seconds at 73° C.

PCR B: primers L2301+V233A, B and 2B. Standard conditions as above.

PCR C: standard C reaction: 20 cycles of (30 seconds at 94° C., 30 seconds at 50° C., and 60 seconds at 73° C.) followed by 600 seconds at 73° C.

The mutation was subcloned as a 330 bp Kpnl-BssHII fragment into pDN1528.

A209V was constructed by the method described by Higuchi et al., 1988:

template: amyL in pDN1528.

PCR A: primers A209V,A and 2C. Conditions: 25 cycles of (30 seconds at 94° C., 30 seconds at 50° C., and 60 seconds at 73° C.) followed by 600 seconds at 73° C.

PCR B: primers A209V,B and IB. Conditions: 25 cycles of (30 seconds at 94° C., 30 seconds at 50° C., and 60 seconds at 73° C.) followed by 600 seconds at 73° C.

PCR C: standard C reaction with only flanking primers: 20 cycles of (30 seconds at 94° C., 30 seconds at 50° C., and 60 seconds at 73° C.) followed by 600 seconds at 73° C.

The mutation was subcloned as a 330 bp Kpnl-BssHII fragment into pDN1528.

Table 1

The following primers have been used for the construction of various variants described above. The 3' end of these primers have identical sequence to parts of pDN1528, and they have all a melting temperature above 50° C.

1B: Corresponds to amino acids: (−20)–(−13), i.e. signal sequence.

5' GGT ACT ATC GTA ACA ATG GCC GAT TGC TGA CGC TGT TAT TTG C 3' (SEQ ID No: 15)

2B: Corresponds to amino acids: 149–155.

5' GGG GTA CTA GTA ACC CGG GCC ATA CAG CGA TTT TAA ATG G 3' (SEQ ID No: 16)

3B: Corresponds to amino acids: 320–326

5' GGG GTA CTA GTA ACC CGG GCC GGT TAC ATT TGT CGA TAA CC 3' (SEQ ID No: 17)

1C: Corresponds to amino acids: 167–161.

5' CTC GTC CCA ATC GGT TCC GTC 3' (SEQ ID No: 18)

2C: Corresponds to amino acids: 345–339.

5' GGC TTA AAC CAT GTT TGG AC 3' (SEQ ID No: 19)

3C (=pUB110ori): Anneals 3' to amyL.

5' CAC TTC AAC GCA CCT TTC AGC 3' (SEQ ID No: 20)

(1–2)*+L3V

#6079

5' CCT CAT TCT GCA GCA GCG GCG GTT AAT GGG ACG CTG ATG CAG 3' (SEQ ID No: 21)

M15T

#6164: 5' GAA TGG TAC ACG CCC AAT GAC GG 3' (SEQ ID No: 22)

#6173: 5' CC GTC ATT GGG CGT GTA CCA TTC 3' (SEQ ID No: 23)

amyL variant III: (1–2)*+L3V+M15T+R23K+S29A+A30E+Y31H+A33S+E34D+H35I

Reg 1A: 5' GCG GAA CAT TTA TCG GAT ATC GGT ATT ACT GCC GTC TGG ATT C 3' (SEQ ID No: 24)

Reg 1B: 5' ATT ACC GAT ATC CGA TAA ATG TTC CGC GTC GTT TTG CAA ACG TTT CCA ATG TTG 3' (SEQ ID No: 25)

E255P

A: GAA AAA ACG GGG AAG CCA ATG TTT ACG GTA GC (SEQ ID No: 26)

B: GC TAC CGT AAA CAT TGG CTT CCC CGT TTT TTC (SEQ ID No: 27)

T341P

CG CTT GAG TCG ACT GTC CAA CCA TGG TTT AAG CCG CTT GC (SEQ ID No: 28)

S373P

A: GG ACG AAA GGA GAC CCC CAG CGC GAA ATT C (SEQ ID No: 29)

B: G AAT TTC GCG CTG GGG GTC TCC TTT CGT CCC G (SEQ ID No: 30)

O374P

A: CG AAA GGA GAC TCC CCT CGC GAA ATT CCT GCC TTG (SEQ ID No: 31)

B: CAA GGC AGG AAT TTC GCG AGG GGA GTC TCC TTT CG (SEQ ID No: 32)

S148N

A: 5' GGG CGC GGC AAC ACA TAC AGC 3' (SEQ ID No: 33)

B: 5' GCT GTA TGT GTT GCC GCG CCC 3' (SEQ ID No: 34)

L230I,V233A

A: 5' C CGG ATT GAT GCT GCG AAA CAC ATT AAA TTT TCT TTT TTG 3' (SEQ ID No: 35)

B: 5' T GTG TTT CGC AGC ATC AAT CCG GAA ACC GTC CAA TTG C 3' (SEQ ID No: 36)

A209V

A: 5' GAC CAT CCT GAC GTC GTA GCA GAA ATT AAG 3' (SEQ ID No: 37)

B: 5'TTC TGC TAC GAC GTC AGG ATG GTC ATA ATC 3' (SEQ ID No: 38)

Example 4

Preparation of the hybrid α-amylase SL68 by DNA fusion

The plasmid used is constructed in a similar way as described for amyL variant III Example 1B) above, except that:

1) reaction A contains plasmid pDN1750, primer SB and primer pUB110ori,
2) reaction B contains plasmid pDN1700, primer SA and primer cat1.
3) reaction A and reaction B are 15 cycles of (60 seconds at 93° C., 60 seconds at 50° C., and 90 seconds at 73° C.) followed by 600 seconds at 73° C. Reaction C is as mentioned above (see Example 1B)).
4) The purified fragment from PCR C is digested consecutively with SphI and partially with EcoRI and the purified 3.3 kb fragment is subcloned into pDN1380 digested to completion with the same restriction endonucleases.

Restriction endonuclease digestion, purification of DNA fragments, ligation, transformation of *B. subtilis*, and DNA sequencing are performed in accordance with well-known techniques. Transformation of *B. subtilis* was performed as described by Dubnau et al. (1971).

Example 5

Fermentation and purification of α-amylase variants

The α-amylase variants encoded by the DNA sequences constructed as described in Examples 1–4 above are produced as follows:

The *B. subtilis* strain harboring the expression plasmid is streaked on a LB-agar plate with 25 mg/ml chloramphenicol from −80° C. stock, and grown overnight at 37° C.

The colonies are transferred to 100 ml BPX media supplemented with 25 mg/ml chloramphenicol in a 500 ml shaking flask.

Composition of BPX medium

| | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| $Na_2HPO_4$, 12 $H_2O$ | 9 g/l |
| Pluronic ™ | 0.1 g/l |

-continued

The culture is shaken at 37° C. at 270 rpm for 5 days.

100–200 ml of the fermentation broth are filtered using a pressure filter with filter aid. After filtration the amylase is precipitated using 80% saturated ammonium sulfate. The precipitate is washed and solubilized and desalted using an Amicon ultrafiltration unit and 25 mM Tris pH 5.6. The desalted sample is subjected to an ion exchange using S-sepharose F.F. The amylase is eluted using a linear gradient of NaCl from 0 to 200 mM. The eluate is desalted using an Amicon unit and applied on a Q-sepharose F.F. at pH 9 in a 25mM Tris buffer. The elution of the amylase is performed using a gradient of 0–200 mM NaCl.

Example 6

Properties of the amyL variant III and amyL variant III+M197T constructed as described in Examples 1 and 2, respectively, were compared.

Determination of oxidation stability

Raw filtered culture broths with amyL variant III and amyL variant III+M197T were diluted to an amylase activity of 100 NU/ml (determined by the α-amylase activity assay described in the Materials and Methods section above) in 50 mM of a Britton-Robinson buffer at pH 9.0 and incubated at 40° C. Subsequently $H_2O_2$ was added to a concentration of 200 mM, and the pH value was re-adjusted to 9.0. The activity was measured after 15 seconds and after 5, 15, and 30 minutes. The amyL variant III+M197T mutant was found to exhibit an improved resistance towards 200 mM $H_2O_2$, pH 9.0 compared to amyL variant III.

Specific activity

The specific activity of Termamyl®, the amyL variant III and the amyL variant III+M197T was determined as described in the Materials and Methods section above. It was found that the specific activity of amyL variant III+M197T was improved by 20% compared to that of amyL variant III. amyL variant III was found to exhibit a 40% higher specific activity compared to Termamyl®.

Furthermore, the specific activity was determined as a function of temperature and pH, respectively. From FIGS. 7 and 8 it is apparent that the amyL variant III+M197T has increased specific activity compared to the parent enzyme (Termamyl®) in the range from pH 4.5 to pH 9.0. Furthermore, the temperature profile has been displaced 10° C. downwards at pH 9. Even though the activity at pH 10.1 is reduced compared to Termamyl®, the performance of amyL variant III in ADD (automatic dishwashing detergent) at 45° C. is highly improved (FIG. 9). This is probably due to the downwards displacement of the temperature profile.

pH/activity profile of amyL variant m and amyL variant III+M197T was determined as described in the Materials and Methods section above, the only difference being that the incubation was performed at 60° C. and at the relevant pH values. The results are apparent from FIG. 5, in which the activity is given as activity per mg enzyme.

Determination of storage stability

The storage stability of α-amylase variant amyL variant III+M197T was determined by adding the variant and its parent α-amylase, respectively, to the detergent in an amount corresponding to a dosage of 0.5 mg enzyme protein per liter of washing liquor (3 liters in the main wash)

together with 12 g of detergent in each wash (1.5 mg enzyme protein). The mixtures were stored at 30° C./60% relative humidity (r.h.) for 0, 1, 2, 3, 4, and 6 weeks. After storage the analytical activity of the samples were determined as well as the performance. The performance was tested by using the whole content of each storage glass (containing enzyme and detergent) in each wash. The soil was corn starch on plates and glasses, and the dishwashing was carried out at 55° C., using a Cylinda 770 machine. The storage stability is illustrated in FIGS. 10 and 11. amyL variant III+M197T was significantly more stable than its parent enzyme.

Example 7

Automatic dishwashing

The dishwashing performance of α-amylase variants of the invention compared to that of their parent α-amylase was evaluated in an automatic dishwashing test.

The α-amylase variants were the amyL variant III, the preparation of which is described in Example 1 above, and the α-amylase variant M197T (prepared by replacing the methionine residue located in position 197 of the *B. licheniformis* α-amylase (SEQ ID No. 2)) with a threonine residue as described in WO 94/02597).

The automatic dishwashing test was performed as described in the Materials and Methods section above.

The results obtained are presented in FIG. 2, from which it is apparent that the amyL variant III and the α-amylase mutant M197T show a substantially improved starch removal, and thus dishwashing performance, relative to that of the parent α-amylase.

Example 8

Laundry washing

The washing performance of the amyL variant m prepared as described in Example 1 and its parent α-amylase was determined under the conditions described in the Material and Methods section above using the following amylase dosages: 0/0.21/0.43/0.86 mg enzyme protein/I.

The results obtained are apparent from FIG. 4. The delta reflectance shown in this figure has been calculated from the reflectance obtained for a swatch having been washed with the relevant enzyme and the reflectance obtained for a swatch washed without enzyme. More specifically, the delta reflectance is the reflectance obtained with enzyme minus the reflectance obtained without enzyme.

From FIG. 4 it is evident that the α-amylase variant of the invention exerts a considerably improved starch removal relative to the parent α-amylase, in other words that the α-amylase variant has an improved washing performance compared to that of the parent α-amylase.

Example 9

The dishwashing performance of a number of the *B. licheniformis* α-amylase variants described in Examples 1–5 was assayed in the mini dishwashing assay described in the Materials and Methods section above.

Some of the variants were tested on different days and, thus, the results obtained for the various α-amylase variants are not directly comparable. However, each variant has been tested against the parent α-amylase and the performance index relative to the parent α-amylase (Termamyl®, index 100) is thus experimentally verified.

It is evident that all variants have an improved dishwashing performance (as measured by their ability to remove starchy stains) as compared to their parent α-amylase.

| | Index |
|---|---|
| *B. licheniformis* amylase variants | |
| Termamyl ® | 100 |
| E255P | 135 |
| T341P | 120 |
| S373P | 125 |
| Q374P | 126 |
| (1-2)* + L3V | 117 |
| S148N | 112 |
| M15T | 115 |
| L230I + V233A | 112 |
| A209V | 118 |
| S29A + A30E + Y31H + A33S + E34D + H35I | 100 |
| Combinations | |
| T341P + Q374P | 117 |
| (1-2)* + L3V + M15T + R23K + S29A + A30E + Y31H + A33S + E34D + H35I | 140 |
| (1-2)* + L3V + M15T + R23K + S29A + A30E + Y31H + A33S + E34D + H35I + E255P | 156 |
| (1-2)* + L3V + M15T + R23K + S29A + A30E + Y31H + A33S + E34D + H35I + M197T | 124 |
| (1-2)* + L3V + M15T + R23K + S29A + A30E + Y31H + A33S + E34D + H35I + E255P + Q374P | 143 |
| (1-2)* + L3V + M15T + R23K + S29A + A30E + Y31H + A33S + E34D + H35I + E255P + Q374P + T341P | 127 |
| (1-2)* + L3V + M15T + R23K + S29A + A30E + Y31H + A33S + E34D + H35I + E255P + M197I | 141 |
| (1-2)* + L3V + M15T + R23K + S29A + A30E + Y31H + A33S + E34D + H35I + E255P + M197N | 124 |
| (1-2)* + L3V + M15T + R23K + S29A + A30E + Y31H + A33S + E34D + H35I + E255P + M197S | 113 |
| (1-2)* + L3V + M15T + R23K + S29A + A30E + Y31H + A33S + E34D + H35I + E255P + M197T | 71 |

Example 10

The washing performance of a number of the *B. licheniformis* α-amylase variants described in Examples 1–5 was tested by means of the laundry washing assay described in the Materials and Methods section above, using the different commercially available detergents mentioned in the tables below.

The IX (dR at c=0.5) is the index (expressed as percentage) obtained by dividing the delta reflectance (see Example 8) for a swatch washed with 0.5 mg/l of the α-amylase variant in question by the delta reflectance for a swatch washed with 0.5 mg/l of Termamyl®. dR at c=0.2 and dR at c=0.1 are the corresponding index (IX) values for enzyme concentrations of 0.2 and 0.1 mg/l, respectively.

It is evident that all variants have an improved washing performance (as measured by their ability to remove starchy stains) relative to their parent α-amylase.

| 5 g/l Ariel Ultra LiquidNo presoak, 40° C., 20 minutes, pH 7 | |
|---|---|
| Enzyme | IX (dR at c = 0.5) |
| Termamyl ® | 100 |
| amyL var. III + M197T | 140 |
| S29A + A30E + Y31H + A33S + E34D + H35I | 103 |
| E458D + P459T + V461K + N463G + E465D | 100 |
| R242P | 106 |
| E255P | 133 |
| M15T | 101 |

| 2 g/l Tide with Bleach Feb 92 No presoak, 40° C., 15 minutes, pH 10 | |
|---|---|
| Enzyme | IX (dR at c = 0.2) |
| Termamyl ® | 100 |
| S29A + A30E + Y31H + A33S + E34D + H35I | 103 |
| E458D + P459T + V461K + N463G + E465D | 122 |
| R242P | 112 |
| E255P | 109 |
| T341P | 108 |
| H450Y | 109 |
| Q374P | 111 |
| M15T | 120 |

| 3 g/l of Bleach containing - Commercial South American HDP DF-931001.1 16 hours presoak, 30° C., 15 minutes, pH 10 | |
|---|---|
| Enzyme | IX (dR at c = 0.1) |
| Termamyl ® | 100 |
| amyL var. III + M197T | 103 |
| amyL var. III + M197L | 111 |
| S29A + A30E + Y31H + A33S + E34D + H35I | 114 |
| E458D + P459T + V461K + N463G + E465D | 109 |
| R242P | 117 |
| E255P | 134 |
| T341P | 116 |
| H450Y | 106 |
| Q374P | 113 |
| M15T | 117 |
| H68Q | 115 |

Example 11

Determination of Vmax Km and V

Km and Vmax of the α-amylases comprising the amino acid sequences SEQ ID Nos. 2, 4 and 6, respectively, and the α-amylase variant m and the hybrid α-amylase SL68 described in Examples 1–4, respectively, were determined as described in the Materials and Methods section above.

The following Vmax and Km values were obtained:

| | Vmax $\frac{\text{mg glucose eqv.}}{\text{mg enzyme x h}}$ | Km mg starch/ml |
|---|---|---|
| SEQ ID No. 6 | 45.0 | 1.47 |
| SEQ ID No. 4 | 11.5 | 1.28 |
| SEQ ID No. 2 | 6.4 | 0.18–0.25 |
| amyL variant III | 8.0 | 0.18–0.25 |
| SL68 | 7.3 | 0.18–0.25 |

The hydrolysis velocity obtained for each of the enzymes may at low substrate concentrations be determined on the basis of the Michaelis-Menten equation $$V=Vmax\times[S]/[S]+Km$$

which, when [S]<<Km may be reduced to V=Vmax×[S]/Km.

From this equation it is apparent that a higher hydrolysis velocity (V) may be obtained when Km is reduced and/or Vmax is increased.

During washing it is reasonable to assume that the substrate concentration is considerable lower than Km and accordingly, based on the above stated values for Km and Vmax, it is possible to determine the hydrolysis velocity of each of the variants listed above. The following values are be found:

| [S] | V, SEQ ID 2 | V, amyL III | V, SL68 |
|---|---|---|---|
| 0.3 | 4.0 | 5 | 4.6 |
| 0.1 | 2.2 | 3 | 2.6 |
| 0.05 | 1.3 | 1.9 | 1.6 |

From the above table it is evident that the hydrolysis velocity of amyL variant III is higher than that of SL68, which again is higher than that of the *B. licheniformis* α-amylase having the amino acid sequence shown in SEQ ID No. 2 (the parent enzyme).

REFERENCES CITED IN THE SPECIFICATION

Suzuki et al., the Journal of Biological Chemistry, Vol. 264, No. 32, Issue of Nov. 15, pp. 18933–18938 (1989).

B. Diderichsen and L. Christiansen, Cloning of a maltogenic α-amylase from *Bacillus stearothermophilus*, FEMS Microbiol. Letters: 56: pp. 53–60 (1988).

Hudson et al., Practical Immunology, Third edition (1989), Blackwell Scientific Publications.

Lipman and Pearson (1985) Science 227, 1435.

Sambrook et al., *Molecular Cloning: A Laboratory Manual,* 2nd Ed., Cold Spring Harbor, 1989.

S. L. Beaucage and M. H. Caruthers, *Tetrahedron Letters* 2, 1981, pp. 1859–1869.

Matthes et al., *The EMBO J.* 3, 1984, pp. 801–805.

R. K. Saiki et al., *Science* 239, 1988, pp. 487–491.

Morinaga et al., 1984, *Biotechnology* 2, pp. 646–639.

Nelson and Long, *Analytical Biochemistry* 180, 1989, pp. 147–151.

Hunkapiller et al., 1984, *Nature* 310, pp. 105–111.

R. Higuchi, B. Krummel, and R. K. Saiki (1988). A general method of in vitro preparation and specific mutagenesis of DNA fragments: study of protein and DNA interactions. *Nucl. Acids Res.* 16, pp. 7351–7367.

Dubnau et al., 1971, *J. Mol. Biol.* 56, pp. 209–221.

Gryczan et al., 1978, *J. Bacteriol.* 134, pp. 318–329.

S. D. Erlich, 1977, *Proc. Natl. Acad. Sci.* 74 pp. 1680–1682.

Boel et al., 1990, *Biochemistry* 29, pp. 6244–6249.

We claim:

1. A variant of a parent *B. licheniformis* alpha-amylase enzyme having an improved washing or dishwashing performance as compared to the parent enzyme, wherein said variant comprises a modification, substitution or deletion of said parent at a position corresponding to SEQ ID No. 2 selected from the group consisting of:

a) at least one of the amino acid residues located in positions 1, 2, 3, 23, or 29–35 of the parent alpha-amylase has been substituted or deleted;

b) in which at least one amino acid has been added to the parent alpha-amylase within the amino acid segment located in positions 29–35;

c) the amino acid residue H68 has been modified;

d) the amino acid residue located at position 104 has been modified;

e) at least one of the amino acid residues located at positions 121 and 128 has been modified;

f) the amino acid residues S187 has been modified;

g) at least one of the amino acid residues L230, V233 or R242 has been modified;

h) at least one of the amino acid residues located at 290 or 293 has been modified;

i) at least one of the amino acid residues T341 has been modified;

j) at least one of the amino acid residues located in the region 370–374 has been modified; and k) at least one of the amino acid residues at A435 or H450 has been modified.

2. The variant according to claim 1 which further comprises the substitution or deletion of an amino acid residue located at position 15.

3. The variant according to claim 1 or 2, in which at least one amino acid residue located in positions 29–35 of the parent alpha-amylase has been substituted or deleted, or in which at least one amino acid has been added to the parent alpha-amylase within the amino acid segment located in positions 29–35.

4. The variant according to claim 1, wherein the parent alpha-amylase is the *B. licheniformis* alpha-amylase has the amino acid sequence shown in SEQ ID No. 2, or an analogue of said alpha-amylase, which is at least 90% homologous with the sequence shown in SEQ ID No. 2.

5. The variant according to claim 2, in which at least one of the following amino acid residues has been modified; A1, N2, L3, R23, S29, A30, Y31, A33, E34, or H35.

6. The variant according to claim 5 which further comprises modification of the amino acid residue at M15.

7. The variant according to claim 5 comprising one of the following mutations: A1V; N2*; L3V; A1*+N2*; S29A; A30E,N; Y31H,N; A33S; E34D,S; H351,L; or R23K,T.

8. The variant according to claim 7 which further comprises the mutation M15T or M15L.

9. The variant according to claim 4 which further comprises the modification of at least one amino acid residue located in positions 142–182.

10. The variant according to claim 1 in which at least one of the amino acid residues located at positions 104 and 128 has been modified.

11. The variant according to claim 1 in which at least one of the amino acid residues D104, D 128 or S187 has been modified.

12. The variant according to claim 11 which further comprises modification of amino acid residues A209 or T217.

13. The variant according to claim 11 which comprises at least one of the mutations, D104N, D128E, or S187D.

14. The variant according to claim 13 which further comprises at least one of the mutations, A209V or T217K.

15. The variant according to claim 1 in which at least one of the amino acid residues L230, V233 or R242 has been modified.

16. The variant according to claim 1 in which at least one of the amino acid residues located in positions 290 or 293 has been modified.

17. The variant according to claim 1 in which at least one of the amino acid residues T341 has been modified.

18. The variant according to claim 1 which comprises the mutation T341P.

19. The variant according to claim 1 in which at least one of the amino acid residue located at positions 370, 371, 372, or 374 has been modified.

20. The variant according to claim 19 which comprises at least one of the following mutations 370*, 371*, 372*, (370–372)*, Q374P.

21. The variant according to claim 1 in which at least one of the amino acid residues A435 or H450 has been modified.

22. The variant according to claim 21 which comprises the mutations A435S or H450Y.

23. The variant according to claim 1 which comprises at least one of the following mutations: R242P, T341P, S373P, Q374P, A420P, or Q482P.

24. The variant according to claim 1 which further comprises a mutation in positions M197 or in position E255.

25. The variant according to claim 24 which comprises at least one of the following mutations: M197T,G,I,A,L,A,S, N,C or E255P.

26. A variant of a parent alpha-amylase derived from *B. licheniformis* comprising one of the following mutations corresponding to positions at SEQ ID No. 2 selected from the group consisting of:

T341P+Q374P;

A1*+N2*+L3V+M15T+R23K+S29A+A30E+Y31H+A33S+E34D+H351+E255P;

A1*+N2*+L3V+M15T+R23K+S29A+A30E+Y31H+A33S+E34D+H35I+M197T;

A1*+N2*+L3V+M15T+R23K+S29A+A30E+Y31H+A33S+E34D+H35I+M197I;

A1*+N2*+L3V+R23K+S29A+A30E+Y31H+A33S+E34D+H35I+M197L;

A1*+N2*+L3V+M15T+R23K+S29A+A30E+Y31H+A33S+E34D+H35I+E255P+Q374P;

A1*+N2*+L3V+M15T+R23K+S29A+A30E+Y31H+A33S+E34D+H35I+E255P+Q374+T341P;

A1*+N2*+L3V+M15T+R23K+S29A+A30E+Y31H+A33S+E34D+H35I+E255P+M197;

A1*+N2*+L3V+M15T+R23K+S29A+A30E+Y31H+A33S+E34D+H35I+E255P+M197N;

A1*+N2*+L3V+M15T+R23K+S29A+A30E+Y31H+A33S+E34D+H35I+E255P+M197S;

A1*+N2*+L3V+M15T+R23K+S29A+A30E+Y31H+A33S+E34D+H35I+E255P+Q347P+T341P+M197I; and

A1*+N2*+L3V+M15T+R23K+S29A+A30E+Y31H+A33S+E34D+H35I+E255P+M197T.

27. The variant according to claim 1 or 26, which is a hybrid alpha-amylase comprising a C-terminal part of an alpha-amylase derived from a strain of *B. licheniformis* and a N-terminal part of an alpha-amylase derived from a strain of *B. amyloliquefaciens* or from a strain of *B. stearothermophilus.*

28. The variant according to claim 27, which comprises at least 430 amino acid residues of the C-terminal part of the *B. licheniformis* alpha-amylase.

29. The variant according to claim 28 comprising (a) an amino acid segment corresponding to the 37 N-terminal amino acid residues of the *B. amyloliquefaciens* alpha-amylase having the amino acid sequence shown in SEQ ID No. 4 and an amino acid segment corresponding to the 445 C-terminal amino acid residues of the *B. licheniformis* alpha-amylase having the amino acid sequence shown in SEQ ID No. 2 or (b) an amino acid segment corresponding to the 68 N-terminal amino acid residues of the *B. stearothermophilus* alpha-amylase having the amino acid sequence shown in SEQ ID No. 6 and an amino acid segment corresponding to the 415 C-terminal amino acid residues of the *B. licheniformis* alpha-amylase having the amino acid sequence shown in SEQ ID No. 2.

30. The alpha-amylase variant according to claim 1 which displays a higher hydrolysis velocity than that of the parent alpha-amylase.

31. A detergent additive comprising an alpha-amylase variant according to claim 1.

32. The detergent additive of claim 31 in which said additive is in the form of a non-dusting granulate, stabilized liquid or protected enzyme.

33. A detergent additive according to claim 31 which contains 0.02–200 mg of enzyme protein/g of the additive.

34. The detergent additive according to claim 31 which additionally comprises another enzyme.

35. The detergent additive according to claim 31 which additionally comprises another enzyme selected from the group consisting of a protease, a lipase, a peroxidase, another amylolytic enzyme and a cellulase.

36. A detergent composition comprising an alpha-amylase variant according to claim 1.

37. A detergent composition according to claim 36 which additionally comprises another enzyme.

38. The detergent composition according to claim 36 which additionally comprises another enzyme selected from the group consisting of a protease, a lipase, a peroxidase, another amylolytic enzyme and a cellulase.

39. A manual or automatic dishwashing detergent composition comprising an alpha-amylase variant according to claim 1.

40. A dishwashing detergent composition according to claim 36 which additionally comprises another enzyme selected from the group consisting of a protease, a lipase, a peroxidase, another amylolytic enzyme and a cellulose.

41. A manual or automatic laundry washing composition comprising an alpha-amylase variant according to claim 1.

42. A laundry washing composition according to claim 41 which additionally comprises another enzyme selected from the group consisting of a protease, a lipase, a peroxidase, an amylolytic enzyme and a cellulase.

* * * * *

UNITED STATES PATENT AND TRADEMARK OFFICE

CERTIFICATE OF CORRECTION

PATENT NO. : 5,830,837

DATED : November 3, 1998

INVENTOR(S) : Bisgard-Frantzen, et al.

It is certified that error appears in the above-identified patent and that said Letters Patent is hereby corrected as shown below:

Col. 72, line 15, claim 26, delete "H351" and insert --H35I--.

Signed and Sealed this

Twenty-sixth Day of December, 2000

*Attest:*

Q. TODD DICKINSON

*Attesting Officer*

*Director of Patents and Trademarks*